US006992094B1

(12) United States Patent
Bernardon et al.

(10) Patent No.: US 6,992,094 B1
(45) Date of Patent: Jan. 31, 2006

(54) DIARYLSELENIDE COMPOUNDS AND THEIR USE IN HUMAN OR VETERINARY MEDICINE AND IN COSMETICS

(75) Inventors: Jean-Michael Bernardon, Le Rouret (FR); Philippe Diaz, Nice (FR)

(73) Assignee: Galderma Research & Development, S.N.C., Valbonne Sophia Antipolis (FR)

(*) Notice: Subject to any disclaimer, the term of this patent is extended or adjusted under 35 U.S.C. 154(b) by 0 days.

(21) Appl. No.: 09/719,219

(22) PCT Filed: Jun. 11, 1999

(86) PCT No.: PCT/FR99/01389

§ 371 (c)(1),
(2), (4) Date: Mar. 28, 2001

(87) PCT Pub. No.: WO99/65872

PCT Pub. Date: Dec. 23, 1999

(30) Foreign Application Priority Data

Jun. 12, 1998 (FR) ................................. 98 07439

(51) Int. Cl.
*A61K 7/40* (2006.01)
*C07D 409/12* (2006.01)

(52) U.S. Cl. ...................................... 514/350; 546/298

(58) Field of Classification Search ................ 546/298; 514/350
See application file for complete search history.

(56) References Cited

FOREIGN PATENT DOCUMENTS

| EP | 0 170 105 | 2/1986 |
|---|---|---|
| EP | 0 661 258 | 7/1995 |
| EP | 0 679 630 | 11/1995 |
| EP | 67-9630 | * 11/1995 |
| WO | WO 92 20643 | 11/1992 |
| WO | WO 93 21146 | 10/1993 |
| WO | WO 94 12880 | 6/1994 |
| WO | 97-16422 | * 5/1997 |
| WO | WO 97 16422 | 5/1997 |
| WO | 98 22423 | 5/1998 |

OTHER PUBLICATIONS

Nakanishi et. al., Inverse Substituent Effect on 77 Se NMR chemical shifts in naphthalene systems with linear 4 C-6e Se4 bond: 1[8-(p-YC6H4Se)ClOH6]SeSe[ClOH6(SeC4y-p)-8']-1, vs. 1-(MeSe)-8-(p-YC6H4Se)CloH6, Chem. Lett. vol. 11, pp. 947-948, vol. 11.*
Oncology, vol. 15, No. 11, Nov. 2001.*
Nakanishi, et. al., "Structure of 1-(Arylselanyl) naphthalenes-Y Dependence in 1-(p-YC6H4Se)C10H7", Eur. J. Org. Chem., 2001, 3933-3943.*

Diaz, "Solution-Phase Synthesis of Diaryl Selenides Using Polymer-Supported Borohydride", Organic Letters, vol. 2, No. 12, pp. 1705-1708, Year 2000.*
Ca 85: 192503, "Some reactions of 1-lithio-2-n-butyl-1,2-dihydropyrine. VI. Synthesis of Beta-substituted pyridines", Knaus et. al.*
Lendaris et al. "Reach through claims . . . " Intellectual property update v. 4, No. 15, (2004).*
Madhaven N. "Amended final report . . . " CA 134:315849 (2000).*
"Retinobenzoic Acids, Structure-Activity Relationships of Aromatic Amides with Retinoidal Activity", J. Med. Chem. 1988, vol. 31, pp. 2182-2192.
"Structural Modifications of 6-Naphthalene-2-Carboxylate Retinoids", Kuo-Long Yu, et al, Bioorganic & Medicinal Chemistry Letters, vol. 6, No. 23, pp. 2865-2870.
"The Retinoid Receptors", Susan M. Pemrick et al, Leukemia, vol. 8, Suppl. 3, 1994, pp. S1-S10.
Eremia, S. et al., "Prevention of Temporal Alopecia Following Rhytidectomy; the Prophylactic Use on Minoxidil. A Study of 60 Patients", Dematol Surg Jan. 2002;28(1):66-74.
Christodoulou, C. et al., "Effectiveness of the MSC Cold Cap System in the Prevention of Chemotherapy-Induced Alopecia", Oncology 2002;62(2):97-102.
Chen, C.H. et al., "Targeting Expression of the Human Vitamin D Receptors to the Keratinocytes of Vitamin D Receptor Null Mice Prevents Alopecia", Endocrinology Dec. 2001; 142(12):5386-9.
Jahnukainen K. et al., "Amifostine Protects Against Early but not Late Toxic Effects of Doxorubicin in Infant Rats", Cancer Res Sep. 1, 2001;61(17):6423-7.
Davis, S.T. et al, "Prevention of Chemotherapy-Induced Alopecia in Rats by CDK Inhibitors", Science Jan. 5, 2001; 291(5501):134-7.
Katsimbri, P. et al., "Prevention of Chemotherapy-Induced Alopecia Using an Effective Scalp Cooling System", Eur J Cancer Apr. 2000; 36(6):766-71.
Hidalgo M. et al., "A Phase I Trial of Topical Topitriol (calcitriol, 1,25-dihydroxyvitamin D3) to Prevent Chemotherapy-Induced Alopecia" Anticancer Drugs Apr. 1990; 10(4):393-5.
Chen, G. et al., "Protection Against Cyclophosphamide-Induced Alopecia and Inhibition of Mammary Tumor Growth by Topical 1,25-dihydroxyvitamin D3 in Mice", Int J Cancer Jan. 19, 1998; 75(2):303-9.

(Continued)

*Primary Examiner*—Celia Chang
(74) *Attorney, Agent, or Firm*—Buchanan Ingersoll, P.C.

(57) ABSTRACT

The invention concerns novel diarylselenide compounds corresponding to the general formula (I) and the use thereof in pharmaceutical compositions in human or veterinary medicine (in the treatment of dermatological, rheumatic, cardiovascular and ophthalmologic pathologies in particular), or in cosmetic compositions.

8 Claims, No Drawings

OTHER PUBLICATIONS

Ron, I.G. et al., Scalp Cooling in the Prevention of Alopecia in Patients Receiving Depilating Chemotherapy, Support Care Cancer Mar. 1997;5(2):136-8.

Lemenager, M. et al., "Effectiveness of Cold Cap in the Prevention of Doxetaxel-Induced Alopecia", Eur J Cancer Feb. 1997;33(2):297-300.

Srendi, B. et al., "Bone Marrow-Sparing and Prevention of Alopecia by AS101 in Non-Small-Cell Lung Cancer Patients Treated with Carboplatin and Etoposide", J Clin Oncol Sep. 1995;13(9):2342-53.

Jimenez, J.J., "Pretreatment with 1,25(OH)2D3 Protects from Cytoxan-Induced Alopecia without Protecting the Leukemic Cells from Cytoxan", Am J Med Sci Aug. 1995; 310(2):43-7.

Hussein, A.M., "Protection Against Cytosine Arabinoside-Induced Alopecia by Minoxidil in a Rat Animal Model", Int J Dermato Jul. 1995;34(7):470-3.

Hussein, A.M. et al., "Protection Against Chemotherapy-Induced Alopecia by Cyclosporin A in the Newborn Rat Animal Model", Dematology 1995;190(3):192-6.

Rodriguez, R. et al., "Minoxidil (Mx) as a Prophylaxis of Doxorubicin-Induced Alopecia", Ann Oncol Oct. 1994;5(8): 769-70.

Balsari, A.L. et al., "Protection Against Doxorubicin-Induced Alopecia in Rats by Liposome-Entrapped Monoclonal Antibodies", FASEB J Feb. 1994;8(2):226-30.

Tollenaar, R.A. et al., "Scalp Cooling Has No Place in the Prevention of Alopecia in Adjuvant Chemotherapy for Breast Cancer", Eur J Cancer 1994;30A(10):1448-53.

Lemenager, M. et al., "Docetaxel-Induced Alopecia Can be Prevented", The Lancet: Letters to the Editor, vol. 346, Aug. 5, 1995, pp. 371-372.

Ramos-e-Silva, M., "Male Pattern Hair Loss: Prevention Rather Than Regrowth", Int J of Dermatology 2000, 39, 728-731.

Fisher, D.A. Deideratum Dermatologica -Wanted: A Dependable and Safe Means to Prevent Alopecia Areata Progression . . . , Int J of Dermatology 1996, 37, 497-499.

Takahata, K. et al., "Protection from Chemotherapy-Induced Alopecia by Docosahexaenoic Acid", Lipids, vol. 34, S105. (1999).

Jimenez, J.J. et al., "Vitamin $D_3$ and Chemotherapy-Induced Alopecia", Nutrition 12:448-453, 1996.

M.F. Boehm et al; Journal of Medicinal Chemistry, vol. 38, 1995, pp. 3146-3155, XP002115271.

* cited by examiner

DIARYLSELENIDE COMPOUNDS AND THEIR USE IN HUMAN OR VETERINARY MEDICINE AND IN COSMETICS

The invention relates, as novel and useful industrial products, to diarylselenide compounds. The invention also relates to the use of these novel compounds in pharmaceutical compositions intended for use in human or veterinary medicine, or alternatively in cosmetic compositions.

The compounds according to the invention have pronounced activity in the fields of cell proliferation and differentiation and find applications more particularly in the topical and systemic treatment of dermatological complaints associated with a keratinization disorder, dermatological (or other) complaints with an inflammatory and/or immunoallergic component, and dermal or epidermal proliferations, whether benign or malignant. These compounds can also be used in the treatment of degenerative diseases of connective tissue, to combat ageing of the skin, whether light-induced or chronological, and to treat cicatrization disorders. They moreover find an application in the ophthalmological field, in particular in the treatment of corneopathies.

The compounds according to the invention can also be used in cosmetic compositions for body and hair hygiene.

The present invention relates to compounds which can be represented by the general formula (I) below:

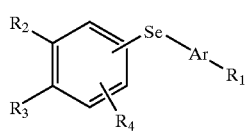

(I)

in which:

$R_1$ represents:
(i) a —$CH_3$ radical,
(ii) a radical —$CH_2$—O—$R_5$,
(iii) a radical —$COR_6$,
$R_5$ and $R_6$ having the meanings given below, Ar represents a radical chosen from the radicals of formulae (a)–(e) below:

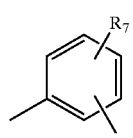

(a)

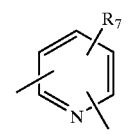

(b)

(c)

(d)

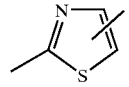

(e)

$R_7$ having the meaning given below, $R_2$ and $R_3$, which may be identical or different, independently represent a radical chosen from:
(i) a hydrogen atom,
(ii) a radical chosen from tert-butyl, 1-methylcyclohexyl and 1-adamantyl radicals,
(iii) a radical —$OR_8$, $R_8$ having the meaning given below,
(iv) a polyether radical, it being understood that at least one of the radicals $R_2$ or $R_3$ represents a radical (ii), $R_2$ and $R_3$ taken together can form, with the adjacent aromatic ring, a 5- or 6-membered saturated ring optionally substituted with methyl groups and/or optionally interrupted with an oxygen or sulphur atom, $R_4$ represents a hydrogen atom, a halogen atom, a lower alkyl radical, a radical $OR_9$, a polyether radical or a radical $COR_{10}$, $R_9$ and $R_{10}$ having the meanings given below, $R_5$ represents a hydrogen atom, a lower alkyl radical or a radical $COR_{11}$, $R_{11}$ having the meaning given below, $R_6$ represents a radical chosen from:
(i) a hydrogen atom,
(ii) a lower alkyl radical,
(iii) a radical $OR_{12}$,
$R_{12}$ having the meaning given below,
(iv) a radical of formula

R' and R" having the meanings given below, $R_7$ represents a hydrogen atom, a halogen atom, a lower alkyl radical, a nitro radical, a radical $OR_{13}$, a polyether radical or a radical of the following formula:

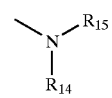

$R_{13}$, $R_{14}$ and $R_{15}$ having the meanings given below, $R_8$ represents a hydrogen atom, a lower alkyl radical, an optionally substituted aryl radical, an optionally substituted aralkyl radical, a monohydroxyalkyl or polyhydroxyalkyl radical or a lower acyl radical, $R_9$ represents a hydrogen atom, a lower alkyl radical, an optionally substituted aryl radical, an optionally substituted aralkyl radical, a monohydroxyalkyl or polyhydroxyalkyl radical, a lower acyl radical, a radical —$(CH_2)n$—$COOR_{16}$ or a radical —$(CH_2)n$—X, n, $R_{16}$ and X having the meanings given below, $R_{10}$ and $R_{11}$, which may be identical or different, represent a lower alkyl radical, $R_{12}$ represents a hydrogen atom, a lower alkyl radical, an optionally substituted aryl or aralkyl radical, a monohydroxyalkyl radical or a polyhydroxyalkyl radical, R' and R", which may be identical or different, represent a hydrogen atom, a lower alkyl radical, an optionally substituted aryl radical or an amino acid residue, or alternatively R' and R" taken together can form, with the nitrogen atom, a heterocycle, $R_{13}$ represents a hydrogen atom or a lower alkyl radical, $R_{14}$ and $R_{15}$, which may be identical or different, represent a hydrogen atom or a lower alkyl radical, $R_{16}$ represents a hydrogen atom or a lower alkyl radical, n represents an integer between 1 and 12 inclusive, X represents a halogen atom.

The invention is also directed towards the salts of the compounds of formula (I) when $R_1$ represents a carboxylic acid function, and the geometrical and optical isomers of the said compounds of formula (I).

When the compounds according to the invention are in the form of salts, they are preferably salts of an alkali metal or alkaline-earth metal, or alternatively of zinc or of an organic amine.

According to the present invention, the expression "lower alkyl radical" means a radical containing from 1 to 6 carbon atoms, and preferably methyl, ethyl, isopropyl, butyl and tert-butyl radicals.

The expression "monohydroxyalkyl radical" means a radical containing from 1 to 6 carbon atoms, in particular a 2-hydroxyethyl, 2-hydroxypropyl or 3-hydroxypropyl radical, it being possible for the monohydroxyalkyl radical to be protected in the form of acetyl or tert-butyldimethylsilyl.

The expression "polyhydroxyalkyl radical" means a radical containing from 2 to 6 carbon atoms and from 2 to 5 hydroxyl groups, such as, in particular, 2,3-dihydroxypropyl, 2,3,4-trihydroxybutyl, 2,3,4,5-tetrahydroxypentyl radicals or a pentaerythritol residue, it being possible for the hydroxyl groups to be protected in the form of acetyls or tert-butyldimethylsilyls.

The expression "optionally substituted aryl radical" means a phenyl radical optionally substituted with at least one halogen atom, a hydroxyl optionally protected in the form of an ether or acetate function, a nitro function or an amino function optionally substituted with an alkyl or acetyl group.

The expression "optionally substituted aralkyl radical" means a benzyl radical or a phenethyl radical optionally substituted with at least one halogen atom, a hydroxyl radical optionally protected in the form of an ether or acetate function, a nitro function or an amino function optionally substituted with an alkyl or acetyl group.

The expression "lower acyl radical" means a radical containing from 1 to 4 carbon atoms, and preferably an acetyl or propionyl radical.

The expression "amino acid residue" means a residue derived, for example, from one of the 20 amino acids of L or D configuration which constitute mammalian proteins.

The term "heterocycle" preferably means a piperidino, morpholino, pyrrolidino or piperazino radical, optionally substituted in position 4 with a $C_1$–$C_6$ alkyl radical or with a mono- or polyhydroxyalkyl radical as defined above.

The expression "polyether radical" means a radical containing from 1 to 6 carbon atoms and from 1 to 3 oxygen or sulphur atoms, such as methoxymethyl ether, methoxyethoxymethyl ether or methylthiomethyl ether radicals.

The expression "halogen atom" preferably means a fluorine, chlorine or bromine atom.

According to the present invention, the compounds of formula (I) that are more particularly preferred are those for which at least one, and preferably all, of the conditions below are satisfied:

$R_1$ represents a radical $COR_6$

Ar represents a radical of formula (a) or (b)

$R_2$ or $R_3$ represents an adamantyl radical or $R_2$ and $R_3$ taken together form, with the adjacent aromatic ring, a 5- or 6-membered saturated ring optionally substituted with methyl groups and/or optionally interrupted with an oxygen or sulphur atom.

Among the compounds of formula (I) above falling within the context of the present invention, mention may be made in particular of the following:

ethyl 4-(3,5,5,8,8-pentamethyl-5,6,7,8-tetrahydro-2-naphthylselanyl)benzoate, 4-(3,5,5,8,8-pentamethyl-5,6,7,8-tetrahydro-2-naphthylselanyl)benzoic acid, ethyl 6-(3,5,5,8,8-pentamethyl-5,6,7,8-tetrahydro- 2-naphthylselanyl)nicotinate, 6-(3,5,5,8,8-pentamethyl-5,6,7,8-tetrahydro-2-naphthylselanyl)nicotinic acid, ethyl 6-(5,5,8,8-tetramethyl-3-propoxy-5,6,7,8-tetrahydro-2-naphthylselanyl)nicotinate, 6-(5,5,8,8-tetramethyl-3-propoxy-5,6,7,8-tetrahydro-2-naphthylselanyl)nicotinic acid, 3-(4-tert-butylphenylselanyl)benzoic acid, 6-(4-tert-butylphenylselanyl)nicotinic acid, 4-(4-tert-butylphenylselanyl)benzoic acid, 4-(4,4-dimethylthiochroman-8-ylselanyl)benzoic acid, 3-(4,4-dimethylthiochroman-8-ylselanyl)benzoic acid, 6-(4,4-dimethylthiochroman-8-ylselanyl)nicotinic acid, 4-(5,5,8,8-tetramethyl-5,6,7,8-tetrahydro-2-naphthylselanyl)benzoic acid, 3-(5,5,8,8-tetramethyl-5,6,7,8-tetrahydro-2-naphthylselanyl)benzoic acid, 6-(5,5,8,8-tetramethyl-5,6,7,8-tetrahydro-2-naphthylselanyl)nicotinic acid, 4-[5-adamantan-1-yl-4-(2-methoxyethoxymethoxy)$_2$-methylphenylselanyl]benzoic acid, 3-[5-adamantan-1-yl-4-(2-methoxyethoxymethoxy)-2-methylphenylselanyl]benzoic acid, 6-(4-methoxyethoxymethoxy-5,5,8,8-tetramethyl-5,6,7,8-tetrahydro-2-naphthylselanyl)nicotinic acid, 3-(4-methoxyethoxymethoxy-5,5,8,8-tetramethyl-5,6,7,8-tetrahydro-2-naphthylselanyl)benzoic acid, 4-(4-methoxyethoxymethoxy-5,5,8,8-tetramethyl- 5,6,7,8-tetrahydro-2-naphthylselanyl)-3-methoxybenzoic acid, 3-(4-methoxyethoxymethoxy-5,5,8,8-tetramethyl-5,6,7,8-tetrahydro-2-naphthylselanyl)-4-methoxybenzoic acid, 6-(4-methoxymethoxy-5,5,8,8-tetramethyl-5,6,7,8-tetrahydro-2-naphthylselanyl)nicotinic acid, 6-(3-methoxyethoxymethoxy-5,5,8,8-tetramethyl-5,6,7,8-tetrahydro-2-naphthylselanyl)nicotinic acid, 2-(3-methoxyethoxymethoxy-5,5,8,8-tetramethyl-5,6,7,8-tetrahydro-2-naphthylselanyl)nicotinic acid, 4-(3-methoxyethoxymethoxy-5,5,8,8-tetramethyl-5,6,7,8-tetrahydro-2-naphthylselanyl)benzoic acid, 3-(3-methoxyethoxymethoxy-5,5,8,8-tetramethyl-5,6,7,8-tetrahydro-2-naphthylselanyl)benzoic acid, 6-(3,5-di-tert-butyl-2-methoxymethoxyphenylselanyl)-nicotinic acid, 2-(3,5-di-tert-butyl-2-methoxymethoxyphenylselanyl)-nicotinic acid, 4-(3,5-di-tert-butyl-2-methoxymethoxyphenylselanyl)-benzoic acid, 3-(3,5-di-tert-butyl-2-methoxymethoxyphenylselanyl)-benzoic acid,
6-[4-adamantan-1-yl-3-benzyloxyphenylselanyl]nicotinic acid,
6-(3,5-di-tert-butyl-2-benzyloxyphenylselanyl)nicotinic acid,
3-methoxy-4-(4-benzyloxy-5,6,7,8-tetrahydro- 5,5,8,8-tetramethyl-2-naphthylselanyl)benzoic acid,
4-(4-benzyloxy-5,6,7,8-tetrahydro-5,5,8,8-tetramethyl-2-naphthylselanyl)benzoic acid,
6-(4-benzyloxy-5,6,7,8-tetrahydro-5,5,8,8-tetramethyl-2-naphthylselanyl)nicotinic acid,
3-methoxy-4-(3-benzyloxy-5,6,7,8-tetrahydro-5,5,8,8-tetramethyl-2-naphthylselanyl)benzoic acid,
6-(3-benzyloxy-5,6,7,8-tetrahydro-5,5,8,8-tetramethyl-2-naphthylselanyl)nicotinic acid,
4-(3-hexyloxy-5,6,7,8-tetrahydro-5,5,8,8-tetramethyl-2-naphthylselanyl)-3-methoxybenzoic acid,
6-(3-hexyloxy-5,6,7,8-tetrahydro-5,5,8,8-tetramethyl-2-naphthylselanyl)nicotinic acid,
4-(5-adamantan-1-yl-4-benzyloxy-2-methylphenylselanyl)-benzoic acid,
6-[3-(5-hydroxypentyloxy)-5,5,8,8-tetramethyl-5,6,7,8-tetrahydro-2-naphthylselanyl]nicotinic acid,
ethyl 4-(5,5,8,8-tetramethyl-5,6,7,8-tetrahydro-2-naphthylselanyl)benzoate,
ethyl 4-(3-methoxyethoxymethoxy-5,5,8,8-tetramethyl-5,6,7,8-tetrahydro-2-naphthylselanyl)benzoate,
ethyl 4-(3-hydroxy-5,5,8,8-tetramethyl-5,6,7,8-tetrahydro-2-naphthylselanyl)benzoate,
4-(3-hydroxy-5,5,8,8-tetramethyl-5,6,7,8-tetrahydro-2-naphthylselanyl)benzoic acid,
ethyl 6-(3-methoxyethoxymethoxy-5,5,8,8-tetramethyl-5,6,7,8-tetrahydro-2-naphthylselanyl)nicotinate,
ethyl 6-(3-hydroxy-5,5,8,8-tetramethyl- 5,6,7,8-tetrahydro-2-naphthylselanyl)nicotinate,
6-(3-hydroxy-5,5,8,8-tetramethyl-5,6,7,8-tetrahydro-2-naphthylselanyl)nicotinic acid,
ethyl 6-[3-(3-ethoxycarbonylpropoxy)-5,5,8,8-tetramethyl-5,6,7,8-tetrahydro-2-naphthylselanyl]nicotinate,
6-[3-(3-carboxypropoxy)-5,5,8,8-tetramethyl-5,6,7,8-tetrahydro-2-naphthylselanyl]nicotinic acid,
ethyl 4-[3-(3-ethoxycarbonylpropoxy)-5,5,8,8-tetramethyl-5,6,7,8-tetrahydro-2-naphthylselanyl]benzoate,
4-[3-(3-carboxypropoxy)-5,5,8,8-tetramethyl-5,6,7,8-tetrahydro-2-naphthylselanyl]benzoic acid,
ethyl 4-[3-(7-methoxycarbonylheptyloxy)-5,5,8,8-tetramethyl-5,6,7,8-tetrahydro-2-naphthylselanyl]benzoate,
4-[3-(7-carboxyheptyloxy)-5,5,8,8-tetramethyl-5,6,7,8-tetrahydro-2-naphthylselanyl]benzoic acid,
ethyl 6-[3-(7-methoxycarbonylheptyloxy)-5,5,8,8-tetramethyl-5,6,7,8-tetrahydro-2-naphthylselanyl]nicotinate,
6-[3-(7-carboxyheptyloxy)-5,5,8,8-tetramethyl-5,6,7,8-tetrahydro-2-naphthylselanyl]nicotinic acid,
ethyl 6-[3-(2-acetoxyethoxy)-5,5,8,8-tetramethyl-5,6,7,8-tetrahydro-2-naphthylselanyl]nicotinate,
6-[3-(2-hydroxyethoxy)-5,5,8,8-tetramethyl-5,6,7,8-tetrahydro-2-naphthylselanyl]nicotinic acid,
ethyl 4-[3-(2-acetoxyethoxy)-5,5,8,8-tetramethyl-5,6,7,8-tetrahydro-2-naphthylselanyl]benzoate,
4-[3-(2-hydroxyethoxy)-5,5,8,8-tetramethyl-5,6,7,8-tetrahydro-2-naphthylselanyl]benzoic acid,
6-(3-adamantan-1-yl-4-methoxyphenylselanyl)nicotinic acid,
[6-(3,5,5,8,8-pentamethyl-5,6,7,8-tetrahydro-2-naphthylselanyl)-3-pyridyl]methanol,
N-ethyl-6-(3,5,5,8,8-pentamethyl-5,6,7,8-tetrahydro-2-naphthylselanyl)nicotinamide,
morpholin-4-yl-[6-(3,5,5,8,8-pentamethyl-5,6,7,8-tetrahydro-2-naphthylselanyl)-3-pyridyl]methanone,
N-(4-hydroxyphenyl)-6-(3,5,5,8,8-pentamethyl-5,6,7,8-tetrahydro-2-naphthylselanyl)nicotinamide,
6-(3,5,5,8,8-pentamethyl-5,6,7,8-tetrahydro-2-naphthylselanyl)pyridine-3-carbaldehyde.

Subjects of the present invention are also processes for preparing the compounds of formula (I), in particular according to the reaction scheme given in FIG. 1.

The derivatives of formula (I) can be obtained (FIG. 1) by a sequence of reactions comprising the action of a lithiated base such as tBuLi on the product (2) in a solvent such as THF, followed by addition of selenium and the formation of the dimer by oxidation in basic medium (EtOH, NaOH). The product (3) obtained is subjected to the action of sodium borohydride in a solvent such as ethanol and then coupled with an iodoaryl in the presence of a nickel catalyst.

When $R_1$ represents a COOH radical, the compounds are prepared by protecting $R_1$ with a protecting group of alkyl type. Saponification of the ester function in the presence of a base, such as sodium hydroxide or lithium hydroxide in an alcoholic solvent or in THF, gives the corresponding acids.

When $R_1$ represents an alcohol radical, the compounds can be obtained from the acid by reduction in the presence of hydride such as boron hydride. The alcohol can be etherified according to the conventional methods.

When $R_1$ represents an aldehyde radical, the compounds can be obtained by oxidation of the corresponding alcohols by the action of manganese oxide or pyridinium dichromate.

When $R_1$ represents an amide radical, the compounds can be obtained by converting the acid into the acid chloride and then by reaction with a suitable amine.

These compounds bind to RXR receptors, some having agonist activity, others having antagonist activity.

The binding and transactivation properties as RXR receptor agonists can be determined by methods known in the art, such as, for example: Levin et al., Nature 1992, 355, 359–61; Allenby et al., Proc. Natl. Acad. Sci., 1993, 90, 30–4.

The RXR-agonist activity can also be determined by the test as described in French patent application No. 95/07301 filed on 19 Jun. 1995 by the Applicant. This test comprises the following steps:

(i) a sufficient amount of a compound which is an active ligand of at least one receptor of the steroidal/thyroid nuclear receptor superfamily, other than an RXR-receptor-specific ligand which can heterodimerize with the RXRs such as an RAR-agonist molecule, is applied topically to an area of skin of a mammal, (ii) a molecule capable of presenting RXR-agonist activity is administered systemically or topically to this same area of mammalian skin before, during or after step (i), and (iii) the response on the area of mammal's skin thus treated is evaluated. Thus, the response to a topical application to a mammals ear of an RAR-agonist molecule which corresponds to an increase in the thickness of this ear can be increased by administering an RXR-receptor-agonist molecule systemically or topically.

The RXRα-antagonist activity can be evaluated in the transactivation test by determination of the dose ($IC_{50}$) which gives 50% inhibition of the transactivating activity of an RXRα-selective agonist: 6-[1-(3,5,5,8,8-pentamethyl-5,6,7,8-tetrahydro-2-naphthyl)cyclopropyl]nicotinic acid (CD 3127) according to the following procedure:

HeLa cells are co-transfected with an expression vector coding for RXRα((p565-RXRα) and a reporter plasmid containing the response element ½ CRBP II cloned upstream of the thymidine kinase heterologous promoter and of the chloramphenicolmacetyl-transferase (CAT) reporter gene. Eighteen hours after co-transfection, the cells are treated with a fixed concentration of CD 3127 and increasing concentrations of the molecule to be evaluated. After treatment for twenty-four hours, the CAT activity is assayed by ELISA. The fixed concentration of CD3127 used is $10^{-8}M$ and corresponds to its $EC_{50}$.

A subject of the present invention is thus, as a medicinal product, the compounds of formula (I) as defined above.

The compounds according to the invention are particularly suitable in the following fields of treatment:

1) for treating dermatological complaints associated with a keratinization disorder which has a bearing on differentiation and on proliferation, in particular for treating common acne, comedones, polymorphonuclear leukocytes, rosacea, nodulocystic acne, acne conglobata, senile acne, secondary acnes such as solar, medication-related or occupational acne,
2) for treating other types of keratinization disorder, in particular ichthyosis, ichthyosiform states, Darier's disease, palmoplantar keratoderma, leucoplasias and leucoplasiform states, and cutaneous or mucous (buccal) lichen,
3) for treating other dermatological complaints associated with a keratinization disorder with an inflammatory and/or immunoallergic component and, in particular, all forms of psoriasis, whether it is cutaneous, mucous or ungual psoriasis and even psoriatic rheumatism, or alternatively cutaneous atopy, such as eczema or respiratory atopy or alternatively gingival hypertrophy; the compounds can also be used in certain inflammatory complaints which have no keratinization disorder,
4) for treating all dermal or epidermal proliferations, whether benign or malignant and whether they are of viral origin or otherwise, such as common warts, flat warts and verruciform epidermodysplasia, oral or florid papillomatoses and proliferations which may be induced by ultraviolet radiation, in particular in the case of basocellular and spinocellular epithelioma,
5) for treating other dermatological disorders such as bullosis and collagen diseases,
6) for treating certain ophthalmological disorders, in particular corneopathies,
7) for repairing or combating ageing of the skin, whether this is light-induced or chronological ageing, or for reducing actinic keratoses and pigmentations, or any pathologies associated with chronological or actinic ageing,
8) for preventing or curing the stigmata of epidermal and/or dermal atrophy induced by local or systemic corticosteroids, or any other form of cutaneous atrophy,
9) for preventing or treating cicatrization disorders or for preventing or repairing stretchmarks, or alternatively for promoting cicatrization,
10) for combating disorders of sebaceous functioning such as the hyperseborrhoea of acne or simple seborrhoea,
11) in the treatment or prevention of cancerous or precancerous states, more particularly promyelocyte leukaemias,
12) in the treatment of inflammatory complaints such as arthritis,
13) in the treatment of any general or skin complaint of viral origin,
14) in the prevention or treatment of alopecia,
15) in the treatment of dermatological or general complaints having an immunological component,
16) in the treatment of complaints of the cardiovascular system such as arteriosclerosis, hypertension, non-insulin-dependent diabetes and obesity,
17) in the treatment of skin disorders due to an exposure to U.V. radiation.

In the therapeutic fields mentioned above, the compounds according to the invention may be employed advantageously in combination with other compounds of retinoid-type activity, with D vitamins or derivatives thereof, with corticosteroids, with anti-free-radical agents, α-hydroxy or α-keto acids or derivatives thereof, or alternatively with ion-channel blockers. The expression "D vitamins or derivatives thereof" means, for example, vitamin $D_2$ or $D_3$ derivatives and in particular 1,25-dihydroxyvitamin $D_3$. The expression "anti-free-radical agents" means, for example, α-tocopherol, superoxide dismutase, ubiquinol or certain metal-chelating agents. The expression "α-hydroxy or α-keto acids or derivatives thereof" means, for example, lactic, malic, citric, glycolic, mandelic, tartaric, glyceric or ascorbic acid salicylic acid derivatives, or the salts, amides or esters thereof. Lastly, the term "ion-channel blockers" means, for example, Minoxidil (2,4-diamino-6-piperidinopyrimidine 3-oxide) and derivatives thereof.

A subject of the present invention is also medicinal compositions containing at least one compound of formula (I) as defined above, one of the optical or geometrical isomers thereof or one of the salts thereof.

A subject of the present invention is thus a novel medicinal composition intended in particular for treating the above-mentioned complaints, and which is characterized in that it comprises, in a pharmaceutically acceptable support which is compatible with the mode of administration selected for this composition, at least one compound of formula (I), one of the optical or geometrical isomers thereof or one of the salts thereof.

The compounds according to the invention may be administered enterally, parenterally, topically or ocularly.

Via the enteral route, the medicinal products may be in the form of tablets, gelatin capsules, sugarcoated tablets, syrups, suspensions, solutions, powders, granules, emulsions, microspheres or nanospheres or polymeric or lipid vesicles which enable controlled release. Via the parenteral route, the compositions may be in the form of solutions or suspensions for infusion or for injection.

The compounds according to the invention are generally administered at a daily dose of about 0.01 mg/kg to 100 mg/kg of body weight taken in 1 to 3 doses.

Via the topical route, the pharmaceutical compositions based on compounds according to the invention are more particularly intended for the treatment of the skin and the mucosae and may thus be in the form of ointments, creams, milks, salves, powders, impregnated pads, solutions, gels, sprays, lotions or suspensions. They may also be in the form of microspheres or nanospheres or polymeric or lipid vesicles or polymeric patches and hydrogels which enable controlled release. These topical-route compositions may either be in anhydrous form or in aqueous form, depending on the clinical indication.

Via the ocular route, they are mainly eyedrops.

These compositions for topical or ocular use contain at least one compound of formula (I) as defined above, or one of the optical or geometrical isomers thereof or alternatively one of the salts thereof, at a concentration preferably of between 0.001% and 5% by weight relative to the total weight of the composition.

The compounds of formula (I) according to the invention also find an application in the cosmetic field, in particular in body and hair hygiene and especially for treating skin types with a tendency towards acne, for promoting the regrowth of the hair, for combating hair loss, for combating the greasy appearance of the skin or the hair, in protection against the harmful effects of the sun or in the treatment of physiologically dry skin types, and for preventing and/or combating light-induced or chronological ageing.

In the cosmetic field, the compounds according to the invention can moreover be employed advantageously in combination with other compounds of retinoid-type activity, with D vitamins or derivatives thereof, with corticosteroids, with anti-free-radical agents, α-hydroxy or α-keto acids or derivatives thereof, or alternatively with ion-channel blockers, all of these various products being as defined above.

The present invention is thus also directed towards a cosmetic composition which is characterized in that it comprises, in a cosmetically acceptable support which is suitable for topical application, at least one compound of formula (I) as defined above or one of the optical or geometrical isomers thereof or one of the salts thereof, it being possible for this cosmetic composition to be, in particular, in the form of a cream, a milk, a lotion, a gel, microspheres or nanospheres or polymeric or lipid vesicles, a soap or a shampoo.

The concentration of compound of formula (I) in the cosmetic compositions according to the invention is advantageously between 0.001% and 3% by weight relative to the composition as a whole.

The medicinal and cosmetic compositions according to the invention can also contain inert additives or even pharmacodynamically or cosmetically active additives or combinations of these additives and, in particular: wetting agents; depigmenting agents such as hydroquinone, azelaic acid, caffeic acid or kojic acid; emollients; moisturizing agents such as glycerol, PEG 400, thiamorpholinone and derivatives thereof, or urea; anti-seborrhoea or anti-acne agents such as S-carboxymethylcysteine, S-benzylcysteamine, the salts and the derivatives thereof, or benzoyl peroxide; antibiotics such as erythromycin and esters thereof, neomycin, clindamycin and esters thereof, and tetracyclines; antifungal agents such as ketoconazole or 4,5-polymethylene-3-isothiazolidones; agents for promoting the regrowth of the hair, such as Minoxidil (2,4-diamino-6-piperidinopyrimidine 3-oxide) and derivatives thereof, Diazoxide (7-chloro-3-methy-1,2,4-benzothiadiazine 1,1-dioxide) and Phenyloin (5,5-diphenylimidazolidine-2,4-dione); non-steroidal anti-inflammatory agents; carotenoids and, in particular, β-carotene; anti-psoriatic agents such as anthraline and derivatives thereof; and, lastly, eicosa-5,8,11,14-tetraynoic acid and eicosa-5,8,11-triynoic acid, the esters and the amides thereof.

The compositions according to the invention may also contain flavour-enhancing agents, preserving agents such as para-hydroxybenzoic acid esters, stabilizing agents, moisture regulators, pH regulators, osmotic pressure modifiers, emulsifying agents, UV-A and UV-B screening agents, and antioxidants such as α-tocopherol, butylhydroxyanisole or butylhydroxytoluene.

Several examples for obtaining active compounds of formula (I) according to the invention, as well as various concrete formulations based on such compounds, will now be given for illustrative purposes and with no limiting nature.

A. EXAMPLES OF COMPOUNDS

Example 1

Ethyl 4-(3,5,5,8,8-pentamethyl-5,6,7,8-tetrahydro-2-naphthylselanyl)benzoate (a) 5,6,7,8-Tetrahydro-3,5,5,8,8-pentamethylnaphthalene-2-diselenide 1.7 M tert-butyllithium in pentane (37.4 mmol, 22 ml) is added to a solution of 2-bromo-5,6,7,8-tetrahydro-3,5,5,8,8-pentamethylnaphthalene (4.4 g, 15.8 mmol) in THF (100 ml) at −78° C. over 10 min. The mixture is stirred at 0° C. for 30 min. Selenium (1.33 g, 16.8 mmol) is added in 2 portions. The mixture is stirred at 0° C. for 15 min and then at room temperature for 30 min. 1N HCl solution (40 ml) is added and the reaction mixture is then treated with ethyl ether. The organic phase is washed twice with water, dried over anhydrous magnesium sulphate and concentrated on a rotary evaporator under vacuum at 40° C. 10 ml of ethanol and 50 mg of sodium hydroxide are added to the oil obtained. The mixture is stirred vigorously for a few minutes in air (until the product has all precipitated) and is then concentrated on a rotary evaporator under vacuum at 40° C. The solid obtained is filtered through silica (eluting with heptane) and then crystallized from an ethanol/ether mixture. Yellow solid. Mass: 3.26 g. Yield: 74%. m.p.: 126° C. 1H NMR (CDCl$_3$): 1.14 (6H, s), 1.23 (6H, s), 1.61 (4H, s), 2.35 (3H, s), 7.05 (1H Ar, s), 7.55 (1H Ar, s).

(b) Ethyl 4-(3,5,5,8,8-pentamethyl-5,6,7,8-tetrahydro-2-naphthylselanyl)benzoate A solution of 5,6,7,8-tetrahydro-3,5,5,8,8-pentamethylnaphthalene-2-diselenide (500 g, 0.89 mmol) and sodium borohydride (68 mg, 1.8 mmol) in 5 ml of ethanol is stirred for 1 hour at room temperature. Ethyl iodobenzoate (440 mg, 1.6 mmol) and bis(bipyridine)nickel(II) bromide (10 mg, 0.016 mmol) (Organometallics 1985, 4, 657–661) are then added. The solution is refluxed for 5 minutes. At room temperature, it is diluted with ethyl ether. The organic phase is washed with water, dried over anhydrous magnesium sulphate and then concentrated. The residue is purified by fast plug (eluent: heptane and then ethyl ether).

White solid. Mass: 495 mg. Yield: 72%. m.p.: 104° C. 1H NMR (CDCl$_3$): 1.22 (6H, s), 1.29 (6H, s), 1.33–1.39 (3H, t), 1.67 (4H, s), 2.32 (3H, s), 4.29–4.38 (2H, q), 7.21–7.26 (3H, c), 7.51 (1H, s), 7.84–7.87 (2H, d).

Example 2

4-(3,5,5,8,8-Pentamethyl-5,6,7,8-tetrahydro-2-naphthylselanyl)benzoic acid

Sodium hydroxide (450 mg, 11.25 mmol) is added to a solution of ethyl 4-(3,5,5,8,8-pentamethyl-5,6,7,8-tetrahydro-2-naphthylselanyl)benzoate (450 mg, 1.04 mmol) in a mixture of 10 ml of THF, 1 ml of methanol and 1 ml of water. The reaction medium is refluxed for 12 h. It is then poured into an ethyl ether/water mixture, acidified to pH 1 with concentrated hydrochloric acid solution and extracted with ethyl ether. After separation of the phases by settling, the organic phase is washed twice with water, dried over anhydrous magnesium sulphate and concentrated on a rotary evaporator under vacuum at 40° C.

White powder. Mass: 371 mg. Yield: 88%. m.p.: 249° C. 1H NMR (CDCl$_3$): 1.21 (6H, s), 1.29 (6H, s), 1.67 (4H, S), 2.32 (3H, s), 7.21–7.24 (2H, d, J=6.9 Hz), 7.38 (1H, s), 7.48 (1H, s), 785–7.88 (2H, d, J=8.35 Hz).

Example 3

Ethyl 6-(3,5,5,8,8-pentamethyl-5,6,7,8-tetrahydro-2-naphthylselanyl)nicotinate

In a manner similar to that of Example 1(b), by reaction of 750 mg (1.33 mmol) of diselenide in 15 ml of ethanol with 102 mg (2.7 mmol) of sodium borohydride, 665 mg (2.4 mmol) of ethyl 6-iodonicotinate and 15 mg (0.024 mmol) of bis(bipyridine)nickel(II) bromide, 779 mg (75%) of the expected derivative are obtained in the form of a white solid. m.p.: 117° C.

$^1$H NMR (CDCl$_3$): 1.25 (6H, s), 1.31 (6H, s), 1.34–1.40 (3H, t), 1.69 (4H, s), 2.37 (3H, s), 4.32–4.40 (2H, q), 6.83–6.87 (1H, d, J=8.3 Hz), 7.28 (1H, s), 7.65 (1H, s), 7.91–7.96 (1H, dd, J=6.10 Hz, J'=2.21 Hz), 8.999–9.00 (1H, d, J=2.14 Hz).

Example 4

6-(3,5,5,8,8-Pentamethyl-5,6,7,8-tetrahydro-2-naphthylselanyl)nicotinic acid

In a manner similar to that of Example 2, by reaction of 750 mg (1.74 mmol) of ethyl 6-(3,5,5,8,8-pentamethyl-5,6,7,8-tetrahydro-2-naphthylselanyl) nicotinate with 700 mg (17.5 mmol) of sodium hydroxide in a THF/methanol/water mixture, 625 mg (89%) of a white cottony product are obtained. m.p.: 258° C. 1H NMR (DMSO): 1.05 (6H, s), 1.11 (6H, s), 1.48 (4H, s) 2.14 (3H, s), 6.79–6.83 (1H, d, J=8.3 Hz), 7.24 (1H, s), 7.45 (1H, s), 7,83–7.88 (1H, dd, J=6.03 Hz, J'=2.3 Hz), 8.69–8.70 (1H, d, J=2.2 Hz), 13.12 (1H, s).

Example 5

Ethyl 6-(5,5,8,8-tetramethyl-3-propoxy-5,6,7,8-tetrahydro-2-naphthylselanyl)nicotinate (a) 1,1,4,4,-Tetramethyl-7-propoxy-1,2,3,4-tetrahydronaphthalene-6-diselenide In a manner similar to that of Example 1(a), by reaction of 6 g (18.5 mmol) of 6-bromo-1,1,4,4-tetramethyl-7-propoxy-1,2,3,4-tetrahydronaphthalene with 1.7 M tert-butyllithium in pentane and selenium in 20 ml of THF, 3.2 g of the expected selenium derivative are obtained in the form of a yellow solid.

m.p.: 92–98° C.

$^1$H NMR (CDCl$_3$): 1.05–1.10 (6H, m), 1.25 (9H, m), 1.55–1.66 (4H, m), 1.86 (2H, sext), 3.98 (2H, t), 6.67 (1H, s), 7.42 (1H, s).

(b) Ethyl 6-(5,5,8,8-tetramethyl-3-propoxy-5,6,7,8-tetrahydro-2-naphthylselanyl)nicotinate In a manner similar to that of Example 1(b), by reaction of 850 mg (1.31 mmol) of diselenide in 85 ml of ethanol with 120 mg (2.62 mmol) of sodium borohydride, 581 mg (2.1 mmol) of ethyl 6-iodonicotinate and 20 mg (0.032 mmol) of bis(bipyridine)nickel(II) bromide, 610 mg (61%) of the expected compound are obtained in the form of white crystals. m.p.: 110–112° C.

$^1$H NMR (CDCl$_3$): 0.81–0,87 (3H, t), 1.24 (6H, s), 1.31 (6H, s), 1.35–1.41 (3H, t), 1.57–1.65 (2H, m), 1.69 (4H, s), 3.87–3.92 (2H, t), 4.32–4.41 (2H, q), 6.66 (1H, s), 7.00–7.03 (1H, d, J=8.3 Hz), 0.7.59 (1H, s), 7.91–7.95 (1H, dd, J=6.2 Hz, J'=2.1 Hz), 8.98–8.99 (1H, d, J=1.7 Hz).

Example 6

6-(5,5,8,8-Tetramethyl-3-propoxy-5,6,7,8-tetrahydro-2-naphthylselanyl)nicotinic acid In a manner similar to that of Example 2, by reaction of 485 mg (1.02 mmol) of ethyl 6-(5,5,8,8-tetramethyl-3-propoxy-5,6,7,8-tetrahydro 2-naphthylselanyl)nicotinate with 385 mg (9.6 mmol) of sodium hydroxide in ethanol (20 ml), 444 mg (97%) of a white solid are obtained. m.p.: 220° C.

Example 7

3-(4-tert-Butylphenylselenalyl)benzoic acid

A mixture of 4-tert-butylphenyl diselenide (0.3 mmol), 480 mg of borohydride polymer supported on Amberlyst IRA 400 resin at 2.5 mmol/g (Aldrich), bis(bipyridine)nickel (II) dibromide (5 mg) (organometallics 1985, 4, 657–661) and ethyl 3-iodobenzoate (0.4 mmol) is heated for 12 h at 67° C. The mixture is filtered and the solution is concentrated. The solid obtained is purified on an SPE cartridge packed with silica gel. The fractions containing the expected product are combined and concentrated under vacuum. The ester is saponified in a mixture of 2.5 ml of THF, 2.5 ml of ethyl alcohol and 0.5 ml of aqueous 33% sodium hydroxide solution. The reaction medium is acidified with HCl solution, extracted with ethyl ether, dried over magnesium sulphate and concentrated to give the expected product. $^1$H NMR/CDCl$_3$: 1.32 (s, 9H); 7.32 to 7.38 (m, 3H); 7.46 (d, 2H); 7.61 (d, 1H); 7.95 (d, 1H); 8.19 (d, 1H).

Example 8

6-(4-tert-Butylphenylselenalyl)nicotinic acid

The product is obtained in a manner similar to that of Example 7, starting with 4-tert-butylphenyl diselenide and ethyl 6-iodonicotinate.

$^1$H NMR/CDCl$_3$: 1.36 (s, 9H); 7.02 (d, 1H); 7.45 (d, 2H); 7.65 (d, 2H); 7.96 (d, 1H); 9.05 (d, 1H).

Example 9

4-(4-tert-Butylphenylselenalyl)benzoic acid

The product is obtained in a manner similar to that of Example 7, starting with 4-tert-butylphenyl diselenide and ethyl 4-iodobenzoate.

$^1$H NMR/CDCl$_3$: 1.34 (s, 9H); 7.35 (d, 2H); 7.39 (d, 2H); 7.54 (d, 2H); 7.92 (d, 2H).

Example 10

4-(4,4-Dimethylthiochroman-8-ylselenalyl)benzoic acid

(a) 2-Bromo-1-(3-methylbut-2-enylthio)benzene 19.30 g (102.0 mmol) of 2-bromothiophenol, 160 ml of DMF and 15.50 g (112.0 mmol) of potassium carbonate are introduced into a three-necked flask. 13 ml (112.0 mmol) of 1-bromo-3-methyl-2-butene are added dropwise and the mixture is stirred at room temperature for two hours. The reaction medium is poured into water and extracted with ethyl acetate, and the organic phase is separated out by settling, washed with water, dried over magnesium sulphate and evaporated. 26.00 g (99%) of the expected compound are collected in the form of an orange-coloured oil.

$^1$H NMR (CDCl$_3$) d 1.65 (s, 3H), 1.73 (s, 3H), 3.56 (d, 2H, J=7.7 Hz), 5.32 (td, 1H, J=7.7/1.4 Hz), 6.96 to 7.06 (m, 1H), 7.22 to 7.26 (m, 2H), 7.52 (d, 1H, J=7.7 Hz).

(b) 4,4-Dimethyl-8-bromothiochroman 26.00 g (102.0 mmol) of 2-bromo-1-(3-methylbut-2-enylthio)benzene, 180 ml of toluene and 23.20 g (122.0 mmol) of para-toluenesulphonic acid are introduced into a three-necked flask. The reaction medium is refluxed for four hours and evaporated to dryness. The residue is taken up in aqueous sodium hydrogen carbonate solution and extracted with ethyl acetate, and the organic phase is separated out by settling, dried over magnesium sulphate and evaporated. The residue obtained is purified by chromatography on a column of silica, eluting with heptane. 20.00 g (76%) of the expected compound are collected in the form of an orange-coloured oil.

$^1$H NMR (CDCl$_3$) d 1.33 (s, 6H), 1.94 (t, 2H, J=6.0 Hz), 3.04 (t, 2H, J=6.1 Hz), 6.89 (t, 1H, J=7.9 Hz), 7.34 (d, 2H, J=7.9 Hz).

(c) 4,4-Dimethylthiochroman-8-diselenide

One crystal of iodine, magnesium (208 mg, 8.56 mmol) and a few drops of a solution of 4,4-dimethyl-8-bromothiochroman (2 g, 7.78 mmol) in ethyl ether (15 ml) are heated until the organomagnesium reagent has been initiated. The rest of the solution is then added dropwise. The reaction medium is heated for 2 h and selenium (615 mg, 7.78 mmol) is then added at room temperature. Stirring is continued for 30 min and 1N HCl solution is then added. The reaction mixture is treated with ethyl ether. The organic phase is washed twice with water, dried over anhydrous magnesium sulphate and concentrated on a rotary evaporator under vacuum at 40° C. Ethanol and sodium hydroxide are added to the oil obtained. The mixture is stirred vigorously for a few minutes and is then concentrated on a rotary evaporator under vacuum at 40° C.

The product is purified on a column of silica (20 dichloromethane/80 heptane).

White solid. Mass: 300 mg. Yield: 15%.

1H NMR (CDCl$_3$): 1.33 (6H, s), 1.96 (2H, m), 3.09 (2H, m), 6.93 (1H Ar, t, J=7.8 Hz), 7.26 (1H Ar, dd, J=7.8 Hz, J=1.3 Hz), 7.47 (1H Ar, dd, J=7.8 Hz, J=1.3 Hz).

(d) 4-(4,4-Dimethylthiochroman-8-ylselenalyl)benzoic acid

The product is obtained in a manner similar to that of Example 7, starting with 4,4-dimethyl-thiochroman-8-diselenide and ethyl 4-iodobenzoate.

$^1$H NMR/CDCl$_3$: 1.36 (s, 6H); 1.95 (m, 2H), 2.99 (m, 2H) 6.99 (t, 1H), 7.31 to 7.46 (m, 4H); 7.91 (d, 2H).

Example 11

3-(4,4-Dimethylthiochroman-8-ylselenalyl)benzoic acid

The product is obtained in a manner similar to that of Example 7, starting with 4,4-dimethylthiochroman-8-diselenide and ethyl 3-iodobenzoate.

$^1$H NMR/CDCl$_3$: 1.35 (s, 6H); 1.95 (m, 2H), 3.02 (m, 2H), 6.94 (t, 1H), 7.18 (dd, 1H); 7.33 to 7.39 (m, 2H), 7.61 (dd, 1H), 8.08 (dd, 1H), 8.16 (d, 1H).

Example 12

6-(4,4-Dimethylthiochroman-8-ylselenalyl)nicotinic acid

The product is obtained in a manner similar to that of Example 7, starting with 4,4-dimethylthiochroman-8-diselenide and ethyl 6-iodonicotinate.

$^1$H NMR/CDCl$_3$: 1.37 (s, 6H); 1.95 (m, 2H), 2.97 (m, 2H), 6.90 (d, 1H), 7.04 (t, 1H); 7.48 to 7.57 (m, 2H), 7.96 (dd, 1H), 9.03 (d, 1H).

Example 13

4-(5,5,8,8-Tetramethyl-5,6,7,8-tetrahydro-2-naphthylselenalyl)benzoic acid

(a) 5,6,7,8-Tetrahydro-5,5,8,8-tetramethylnaphthalene-2-diselenide

A 1.7 M solution of tert-butyllithium in pentane (37.4 mmol, 22 ml) is added to a solution of 2-bromo-5,6,7,8-tetrahydro-5,5,8,8-tetramethyl-naphthalene (4.22 g, 15.8 mmol) in THF (100 ml) at −78° C. over 10 min. The mixture is stirred at 0° C. for 30 min. Selenium (1.33 g, 16.8 mmol) is added in 2 portions. The mixture is stirred at 0° C. for 15 min and then at room temperature for 30 min. 1N HCl solution (40 ml) is added and the reaction mixture is then treated with ethyl ether. The organic phase is washed twice with water, dried over anhydrous magnesium sulphate and concentrated on a rotary evaporator under vacuum at 40° C. 10 ml of ethanol and 50 mg of sodium hydroxide are added to the oil obtained. The mixture is stirred vigorously for a few minutes in air (until all the product has precipitated) and is then concentrated on a rotary evaporator under vacuum at 40° C. The solid obtained is filtered off on silica (eluting with heptane) and is then crystallized from an ethanol/ether ixture.

Orange solid. Mass: 2.9 g. Yield: 69%.

$^1$H NMR (CDCl$_3$): 1.21 (6H, s), 1.25 (6H, s), 1.65 (4H, s), 7.20 (1H Ar, d, J=8.25 Hz), 7.38 (1H Ar, dd, J=1.9 Hz, J=8.25 Hz), 7.51 (1H Ar, d, J=1.9 Hz).

(b) 4-(5,5,8,8-Tetramethyl-5,6,7,8-tetrahydro-2-naphthylselenalyl)benzoic acid

The product is obtained in a manner similar to that of Example 7, starting with 5,6,7,8-tetrahydro-5,5,8,8-tetramethylnaphthalene-2-diselenide and ethyl 4-iodobenzoate.

$^1$H NMR/CDCl$_3$: 1.26 (s, 6H); 1.30 (s, 6H), 1.70 (s, 4H), 7.27 to 7.37 (m, 4H), 7.54 (d, 1 h), 7.91 (d, 2H).

Example 14

3-(5,5,8,8-Tetramethyl-5,6,7,8-tetrahydro-2-naphthylselenalyl)benzoic acid

The product is obtained in a manner similar to that of Example 7, starting with 5,6,7,8-tetrahydro-5,5,8,8-tetramethylnaphthalene-2-diselenide and ethyl 4-iodobenzoate.

$^1$H NMR/CDCl$_3$: 1.25 (s, 6H); 1.27 (s, 6H), 1.68 (s, 4H), 7.24 to 7.26 (m, 2H), 7.34 (t, 1H), 7.48 (s, 1H), 7.60 (dd, 1H), 7.94 (dd, 1H), 8.19 (d, 1H).

Example 15

6-(5,5,8,8-Tetramethyl-5,6,7,8-tetrahydro-2-naphthylselenalyl)nicotinic acid

The product is obtained in a manner similar to that of Example 7, starting with 5,6,7,8-tetrahydro-5,5,8,8-tetramethylnaphthalene-2-diselenide and ethyl 6-iodonicotinate.

$^1$H NMR/CDCl$_3$: 1.29 (s, 6H); 1.32 (s, 6H), 1.72 (s, 4H), 7.03 (s, 1H), 7.36 (d, 1H), 7.45 (dd, 1H), 7.65 (d, 1H), 7.99 (dd, 1H), 9.07 (d, 1H).

Example 16

4-[5-Adamantan-1-yl-4-(2-methoxyethoxymethoxy)-2-methylphenylselenalyl)benzoic acid a) 5-Adamantan-1-yl-4-(2-methoxyethoxymethoxy)-2-methylphenyl diselenide A small portion of a solution of 2-(adamantan-1-yl)-4-bromo-5-methyl-1-methoxyethoxymethoxyphenyl (17 g, 41.5 mmol) in THF (160 ml) is poured onto a mixture of magnesium (1.51 g) and one crystal of iodine, with gentle heating. When the reaction medium decolourizes, the rest of the solution is added so as to maintain a gentle reflux. After the end of the addition, the solution is refluxed for 1 h. After cooling to room temperature, 3.6 g of selenium are added. The reaction medium is stirred for 3 h at room temperature and 1N hydrochloric acid solution (105 ml) and ethyl ether are then added to the reaction medium. The organic phase is washed with water, dried over magnesium sulphate and concentrated on a rotary evaporator. Sodium hydroxide (131 mg) and ethanol (27 ml) are then added. The suspension is stirred in air and at room temperature for 12 h. The product is purified by filtration on silica, eluting with dichloromethane. 12 g (71%) of a yellow solid are obtained. m.p.=101° C.

1H NMR/CDCl$_3$: 1.73 (s, 6H); 2.00 (s, 9H); 2.30 (s, 3H); 3.40 (s, 3H); 3.59 (m, 2H); 3.83 (m, 2H); 5.29 (s, 2H); 6.95 (s, 1H); 7.48 (s, 1H).

b) 4-[5-Adamantan-1-yl-4-(2-methoxyethoxymethoxy)-2-methylphenylselenalyl)benzoic acid The product is obtained in a manner similar to that of Example 7, starting with 5-adamantan-1-yl-4-(2-methoxyethoxymethoxy)-2-methylphenyl diselenide and ethyl 4-iodobenzoate.

$^1$H NMR/CDCl$_3$: 1.75 (s, 6H); 2.07 (s, 9H), 2.34 (s, 3H) 3.42 (s, 3H), 3.62 (m, 2H), 3.89 (m, 2H), 5.35 (s, 2H), 7.14 (s, 1H), 7.19 (d, 2H), 7.50 (s, 1H), 7.87 (d, 2H).

Example 17

3-[5-Adamantan-1-yl-4-(2-methoxyethoxymethoxy)-2-methylphenylselenalyl]benzoic acid The product is obtained in a manner similar to that of Example 7, starting with 5-adamantan-1-yl-4-(2-methoxyethoxymethoxy)-2-methylphenyl diselenide and ethyl 3-iodobenzoate.

$^1$H NMR/CDCl$_3$: 1.75 (s, 6H); 2.06 (s, 9H), 2.34 (s, 3H), 3.41 (s, 3H), 3.62 (m, 2H), 3.87 (m, 2H), 5.34 (s, 2H), 7.10 (s, 1H), 7.28 (t, 1H), 7.38 (dd, 1H), 7.47 (s, 1H), 7.87 (dd, 1H), 8.02 (d, 1H).

Example 18

6-(4-Methoxyethoxymethoxy-5,5,8,8-tetramethyl-5,6,7,8-tetrahydro-2-naphthylselanyl)nicotinic acid a) 4-Methoxyethoxymethoxy-5,6,7,8-tetrahydro-5,5,8,8-tetramethylnaphthalene-2-diselenide In a manner similar to that of Example 1(a), starting with 2-bromo-5,5,8,8-tetramethyl-4-methoxyethoxymethoxy-5,6,7,8-tetrahydronaphthalene, the expected compound is obtained in the form of an orange oil.

b) 6-(4-Methoxyethoxymethoxy-5,5,8,8-tetramethyl5,6,7,8-tetrahydro-2-naphthylselanyl)nicotinic acid The product is obtained in a manner similar to that of Example 7, starting with 4-methoxyethoxymethoxy-5,6,7,8-tetrahydro-5,5,8,8-tetramethylnaphthalene-2-diselenide and ethyl 6-iodonicotinate.

$^1$H NMR/CDCl$_3$: 1.27 (s, 6H); 1.42 (s, 6H); 1.67 (m, 4H) 3.36 (s, 3H), 3.56 (m, 2H), 3.82 (m, 2H), 5.29 (s, 2H), 7.11 (d, 1H), 7.31 (d, 1H), 7.35 (d, 1H), 8.00 (dd, 1H), 9.06 (d, 1H).

Example 19

3-(4-Methoxyethoxymethoxy-5,5,8,8-tetramethyl-5,6,7,8-tetrahydro-2-naphthylselanyl)benzoic acid The product is obtained in a manner similar to that of Example 7, starting with 4-methoxyethoxymethoxy-5,6,7,8-tetrahydro-5,5,8,8-tetramethylnaphthalene-2-diselenide and ethyl 3-iodobenzoate.

$^1$H NMR/CDCl$_3$: 1.26 (s, 6H); 1.38 (s, 6H), 1.62 (m, 4H), 3.36 (s, 3H), 3.53 (m, 2H), 3.78 (m, 2H), 5.22 (s, 2H), 7.12 (d, 1H), 7.15 (d, 1H), 7.35 (t, 1H), 7.65 (dd, 1H), 7.96 (dd, 1H), 8.20 (d, 1H).

Example 20

4-(4-Methoxyethoxymethoxy-5,5,8,8-tetramethyl-5,6,7,8-tetrahydro-2-naphthylselanyl)-3-methoxybenzoic acid

The product is obtained in a manner similar to that of Example 7, starting with 4-methoxyethoxymethoxy-5,6,7,8-tetrahydro-5,5,8,8-tetramethylnaphthalene-2-diselenide and ethyl 4-iodo-3-methoxybenzoate.

$^1$H NMR/CDCl$_3$: 1.26 (s, 6H); 1.42 (s, 6H), 1.66 (m, 4H), 3.35 (s, 3H), 3.54 (m, 2H), 3.81 (m, 2H), 3.98 (s, 3H), 5.27 (s, 2H), 6.94 (d, 1H), 7.25 (d, 1H), 7.30 (d, 1H), 7.48 to 7.53 (m, 2H).

Example 21

3-(4-Methoxyethoxymethoxy-5,5,8,8-tetramethyl-5,6,7,8-tetrahydro-2-naphthylselanyl)-4-methoxybenzoic acid

The product is obtained in a manner similar to that of Example 7, starting with 4-methoxyethoxymethoxy-5,6,7,8-tetrahydro-5,5,8,8-tetramethylnaphthalene-2-diselenide and ethyl 3-iodo-4-methoxybenzoate.

$^1$H NMR/CDCl$_3$: 1.25 (s, 6H); 1.40 (s, 6H), 1.65 (m, 4H), 3.34 (s, 3H), 3.53 (m, 2H), 3.80 (m, 2H), 3.97 (s, 3H), 5.26 (s, 2H), 6.88 (d, 1H), 7.21 (d, 1H), 7.24 (d, 1H), 7.82 (d, 1H), 7.94 (dd, 1H).

Example 22

6-(4-Methoxymethoxy-5,5,8,8-tetramethyl-5,6,7,8-tetrahydro-2-naphthylselanyl)nicotinic acid a) 4-Methoxymethoxy-5,6,7,8-tetrahydro-5,5,8,8-tetramethylnaphthalene-2-diselenide In a manner similar to that of Example 1(a), starting with 2-bromo-5,5,8,8-tetramethyl-4-methoxymethoxy-5,6,7,8-tetrahydronaphthalene, the expected compound is obtained in the form of an orange oil.

b) 6-(4-Methoxymethoxy-5,5,8,8-tetramethyl-5,6,7,8-tetrahydro-2-naphthylselanyl)nicotinic acid The product is obtained in a manner similar to that of Example 7, starting with 4-methoxymethoxy5,6,7,8-tetrahydro-5,5,8,8-tetramethylnaphthalene-2 diselenide and ethyl 6-iodonicotinate.

$^1$H NMR/CDCl$_3$: 1.27 (s, 6H); 1.43 (s, 6H), 1.67 (m, 4H), 3.49 (s, 3H), 5.20 (s, 2H), 7.11 (d, 1H), 7.24 (d, 1H), 7.35 (d, 1H), 8.01 (dd, 1H), 9.07 (d, 1H).

Example 23

6-(3-Methoxyethoxymethoxy-5,5,8,8-tetramethyl-5,6,7,8-tetrahydro-2-naphthylselanyl)nicotinic acid a) 3-Methoxyethoxymethoxy-5,6,7,8-tetrahydro-5,5,8,8-tetramethylnaphthalene-2-diselenide In manner similar to that of Example 1(a), starting with 2-bromo-5,5,8,8-tetramethyl-3-methoxyethoxymethoxy-5,6,7,8-tetrahydronaphthalene, the expected compound is obtained in the form of an orange oil.

b) 6-(3-Methoxyethoxymethoxy-5,5,8,8-tetramethyl-5,6,7,8-tetrahydro-2-naphthylselanyl)nicotinic acid The product is obtained in a manner similar to that of Example 7, starting with 3-methoxyethoxymethoxy-5,6,7,8-tetrahydro-5,5,8,8-tetramethylnaphthalene-2-diselenide and ethyl 6-iodonicotinate.

$^1$H NMR/CDCl$_3$: 1.25 (s, 6H); 1.31 (s, 6H), 1.69 (s, 4H), 3.36 (s, 3H), 3.51 (m, 2H), 3.74 (m, 2H), 5.22 (s, 2H), 7.04 (d, 1H), 7.23 (s, 1H), 7.61 (s, 1H), 7.97 (dd, 1H), 9.05 (d, 1H).

Example 24

2-(3-Methoxyethoxymethoxy-5,5,8,8-tetramethyl-5,6,7,8-tetrahydro-2-naphthylselanyl)nicotinic acid

The product is obtained in a manner similar to that of Example 7, starting with 3-methoxyethoxymethoxy-5,6,7,8-tetrahydro-5,5,8,8-tetramethylnaphthalene-2-diselenide and ethyl 2-iodonicotinate.

$^1$H NMR/CDCl$_3$: 1.25 (s, 6H); 1.31 (s, 6H), 1.68 (s, 4H), 3.37 (s, 3H), 3.52 (m, 2H), 3.74 (m, 2H), 5.17 (s, 2H), 7.10 (dd, 1H), 7.22 (s, 1H), 7.54 (s, 1H), 8.29 (dd, 1H), 8.44 (dd, 1H).

Example 25

4-(3-Methoxyethoxymethoxy-5,5,8,8-tetramethyl-5,6,7,8-tetrahydro-2-naphthylselanyl)benzoic acid

The product is obtained in a manner similar to that of Example 7, starting with 3-methoxyethoxymethoxy-5,6,7,8-tetrahydro-5,5,8,8-tetramethylnaphthalene-2-diselenide and ethyl 4-iodobenzoate.

$^1$H NMR/CDCl$_3$: 1.19 (s, 6H); 1.29 (s, 6H), 1.63 (s, 4H), 3.36 (s, 3H), 3.50 (m, 2H), 3.71 (m, 2H), 5.22 (s, 2H), 7.16 (s, 1H), 7.36 (s, 1H), 7.41 (d, 2H), 7.93 (d, 2H).

Example 26

3-(3-Methoxyethoxymethoxy-5,5,8,8-tetramethyl-5,6,7,8-tetrahydro-2-naphthylselanyl)benzoic acid

The product is obtained in a manner similar to that of Example 7, starting with 3-methoxyethoxymethoxy-5,6,7,8-tetrahydro-5,5,8,8-tetramethylnaphthalene-2-diselenide and ethyl 3-iodobenzoate.

$^1$H NMR/CDCl$_3$: 1.12 (s, 6H); 1.27 (s, 6H), 1.63 (m, 4H), 3.37 (s, 3H), 3.52 (m, 2H), 3.77 (m, 2H), 5.26 (s, 2H), 7.12 (s, 1H), 7.13 (s, 1H), 7.38 (t, 1H), 7.69 (dd, 1H), 7.99. (dd, 2H), 8.25 (d, 1H).

Example 27

6-(3,5-Di-tert-butyl-2-methethoxthoxyphenylselanyl)-nicotinic acid a) 2-Bromo-4,6-di-tert-butyl-1-methoxymethoxyphenyl

A mixture of 2-bromo-4,6-di-tert-butylphenol (4.4 mmol), caesium carbonate (2.95 g) and methoxymethyl chloride (4.8 mmol) in DMF (18 ml) is stirred at room temperature for 24 h. The reaction medium is extracted with ethyl ether. The organic phase is washed with water, dried over magnesium sulphate and concentrated on a rotary evaporator. The product is purified by filtration on silica.

b) 4,6-Di-tert-butyl-1-methoxymethoxyphen-2-yl diselenide

In a manner similar to that of Example 10(c), starting with 10 g of the product obtained above, 1.1 g of magnesium and 2.63 g of selenium, 7.6 g (76%) of the expected product are obtained in the form of a yellow solid.
$^1$H NMR/CDCl$_3$: 1.18 (s, 9H); 1.42 (s, 9H); 3.68 (s, 3H) 5.08 (s, 2H); 7.23 (d, 1H); 7.54 (d, 1H).

c) 6-(3,5-Di-tert-butyl-2-methoxymethoxyphenylselanyl) nicotinic acid

The product is obtained in a manner similar to that of Example 7, starting with 4,6-di-tert-butyl]-methoxymethoxyphen-2-yl diselenide and ethyl 6-iodonicotinate.
$^1$H NMR/CDCl$_3$: 1.30 (s, 9H); 1.45 (s, 9H); 3.51 (s, 3H) 5.17 (s, 2H); 6.94 (d, 1H); 7.50 (d, 1H), 7.56 (d, 1H), 7.98 (dd, 1H), 9.05 (d, 1H).

Example 28

2-(3,5-Di-tert-butyl-2-methoxymethoxyphenylselanyl)-nicotinic acid

The product is obtained in a manner similar to that of Example 7, starting with 4,6-di-tert-butyl-1-methoxymethoxyphen-2-yl diselenide and ethyl 2-iodonicotinate.
$^1$H NMR/CDCl$_3$: 1.30 (s, 9H); 1.46 (s, 9H); 3.51 (s, 3H); 5.16 (s, 2H); 7.12 (dd, 1H); 7.44 (s, 1H), 8.30 (dd, 1H), 8.46 (dd, 1H).

Example 29

4-(3,5-Di-tert-butyl-2-methoxymethoxyphenylselanyl)-benzoic acid

The product is obtained in a manner similar to that of Example 7, starting with 4,6-di-tert-butyl-1-methoxymethoxyphen-2-yl diselenide and ethyl 4-iodobenzoate.

$^1$H NMR/CDCl$_3$: 1.25 (s, 9H); 1.44 (s, 9H); 3.55 (s, 3H) 5.15 (s, 2H); 7.33 to 7.41 (m, 3H); 7.92 (d, 2H).

Example 30

3-(3,5-Di-tert-butyl-2-methoxymethoxyphenylselanyl)benzoic acid

The product is obtained in a manner similar to that of Example 7, starting with 4,6-di-tert-butyl]-methoxymethoxyphen-2-yl diselenide and ethyl 3-iodobenzoate.
$^1$H NMR/CDCl$_3$: 1.20 (s, 9H); 1.44 (s, 9H); 3.60 (s, 3H); 5.17 (s, 2H); 7.15 (d, 1H), 7.32 to 7.36 (m, 2H), 7.56 (dd, 1H); 7.96 (dd, 1H), 8.18 (d, 1H).

Example 31

6-[4-Adamantan-1-yl-3-benzyloxyphenylselenalyl]-nicotinic acid a) 2-(Adamantan-1-yl)-5-bromo-1-(2-methoxyethoxymethoxy)-phenyl

60% sodium hydride (2.5 g) is added portionwise to a solution of 2-(adamantan-1-yl)$_5$-bromo-1-phenol (20.9 g) in a mixture of THF and DMF (5/5). Stirring is continued for 30 min at room temperature after the end of the addition, and methoxyethoxymethyl chloride (8.92 g) is then added. The reaction medium is stirred for 4 h at room temperature and is then treated with water and ethyl ether. The organic phase is washed with water, dried over magnesium sulphate and concentrated. After filtration on silica, 17 g (64%) of the expected product are obtained in the form of a white solid. m.p.=88° C.

b) 4-Adamantan-1-yl-3-(2-methoxyethoxymethoxy)phenyl diselenide

In a manner similar to that of Example 1(a), starting with 13.04 g of 2-(adamantan-1-yl)-5-bromo-1-methoxyethoxymethoxyphenyl, 9.9 g (76%) of the expected product are obtained in the form of a yellow oil.
$^1$H NMR/CDCl3: 1.55 (s, 6H); 2.05 (d, 9H); 3.38 (s, 3H); 3.57 (m, 2H); 3.82 (m, 2H); 5.27 (s, 2H), 7.11 (d, 1H); 7.22 (dd, 1H); 7.38 (d, 1H).

c) 4-Adamantan-1-yl-3-hydroxyphenyl diselenide

A mixture of the product obtained above (200 mg), concentrated sulphuric acid (1.4 ml), methanol (20 ml) and THF (20 ml) is stirred for 12 h at room temperature. The reaction medium is extracted with ethyl acetate. The organic phase is washed twice with water, dried over magnesium sulphate and concentrated on a rotary evaporator under vacuum. The expected product is purified by flash chromatography to give an orange-coloured powder.

d) 4-Adamantan-1-yl-3-benzyloxyphenyl diselenide

A mixture of the product obtained above (4.4 mmol), caesium carbonate (2.95 g) and benzyl chloride (1.3 ml) in DMF (18 ml) is stirred at room temperature for 24 h. The reaction medium is extracted with ethyl ether. The organic phase is washed with water, dried over magnesium sulphate and concentrated on a rotary evaporator. The product is purified by filtration on silica (heptane and then dichloromethane). The expected compound is obtained in the form of a yellow powder.

e) 6-[4-Adamantan-1-yl-3-benzyloxyphenylselenalyl]nicotinic acid

The product is obtained in a manner similar to that of Example 7, starting with 4-adamantan-1-yl-3-benzyloxyphenyl diselenide and ethyl 6-iodonicotinate.
$^1$H NMR/CDCl$_3$, acetone D$_6$: 1.74 (s, 6H); 2.06 (s, 3H) 2.17 (s, 6H); 5.12 (s, 2H); 6.97 (d, 1H), 7.26 to 7.48 (m, 8H), 7.95 (dd, 1H), 9.04 (d, 1H).

Example 32

6-(3,5-Di-tert-butyl-2-benzyloxyphenylselanyl)nicotinic acid a) 3,5-Di-tert-butyl-2-benzyloxyphenyl diselenide

The procedure is identical to that followed for Example 31(c) and 31(d), applied to the product of Example 27(b).

b) 6-(3,5-Di-tert-butyl-2-benzyloxyphenylselanyl)-
nicotinic acid

The product is obtained in a manner similar to that of Example 7, starting with 3,5-di-tert-butyl-2-benzyloxyphenyl diselenide and ethyl 6-iodonicotinate.

$^1$H/CDCl$_3$, acetone D$_6$: 1.33 (s, 9H); 1.44 (s, 9H); 5.13 (s, 2H); 7.00 (d, 1H); 7.24 to 7.32 (m, 5H), 7.51 (d, 1H), 7.60 (d, 1H), 7.98 (dd, 1H), 9.01 (d, 1H).

Example 33

3-Methoxy-4-(4-benzyloxy-5,6,7,8-tetrahydro-5,5,8,8-tetramethyl-2-naphthylselanyl)benzoic acid a) 4-Hydroxy-5,6,7,8-tetrahydro-5,5,8,8-tetramethylnaphthalene-2-diselenide The product of Example 22(a), 4-methoxymethoxy-5,6,7,8-tetrahydro-5,5,8,8-tetramethylnaphthalene-2-diselenide (12.4 g), is treated in a manner similar to that of Example 15(b) to give 11 g (100%) of the expected compound in the form of a yellow solid. m.p.=200° C.

$^1$H NMR/CDCl$_3$: 1.22 (s, 6H); 1.42 (s, 6H); 1.63 (m, 4H) 5.25 (s, 1H); 6.75 (d, 1H); 7.11 (d, 1H).

b) 4-Benzyloxy-5,6,7,8-tetrahydro-5,5,8,8-tetramethylnaphthalene-2-diselenide

A mixture of the product obtained above (2.5 g, 4.4 mmol), caesium carbonate (2.95 g) and benzyl chloride (1.3 ml) in DMF (18 ml) is stirred at room temperature for 24 h. The reaction medium is extracted with ethyl ether. The organic phase is washed with water, dried over magnesium sulphate and concentrated on a rotary evaporator. The product is purified by filtration on silica (heptane and then dichloromethane). 2.1 g (63%) of the expected compound are obtained in the form of a yellow powder.

$^1$H NMR/CDCl$_3$: 1.21 (s, 6H); 1.34 (s, 6H); 1.59 (m, 4H); 4.96 (s, 2H); 7.02 (d, 1H); 7.21 (d, 1H); 7.29 to 7.41 (m, 5H).

c) 3-Methoxy-4-(4-benzyloxy-5,6,7,8-tetrahydro-5,5,8,8-tetramethyl-2-naphthylselanyl)benzoic acid The product is obtained in a manner similar to that of Example 7, starting with 4-benzyloxy-5,6,7,8-tetrahydro-5,5,8,8-tetramethylnaphthalene-2-diselenide and ethyl 4-iodo-3-methoxybenzoate.

$^1$H NMR/CDCl$_3$: 1.27 (s, 6H), 1.43 (s, 6H), 1.66 (m, 4H) 3.98 (s, 3H), 5.04 (s, 2H), 6.88 (d, 1H), 7.01 (d, 1H), 7.29 (s, 1H), 7.33 to 7.52 (m, 7H).

Example 34

4-(4-Benzyloxy-5,6,7,8-tetrahydro-5,5,8,8-tetramethyl-2-naphthylselanyl)benzoic acid The product is obtained in a manner similar to that of Example 7, starting with 4-benzyloxy5,6,7,8-tetrahydro-5,5,8,8-tetramethylnaphthalene-2-diselenide and ethyl 4-iodobenzoate.

$^1$H NMR/CDCl$_3$: 1.26 (s, 6H), 1.41 (s, 6H), 1.65 (m, 4H), 5.02 (s, 2H), 6.92 (d, 1H), 7.22 (d, 1H), 7.31 to 7.41 (m, 7H), 7.90 (d, 2H).

Example 35

6-(4-Benzyloxy-5,6,7,8-tetrahydro-5,5,8,8-tetramethyl-2-naphthylselanyl)nicotinic acid The product is obtained in a manner similar to that of Example 7, starting with 4-benzyloxy5,6,7,8-tetrahydro-5,5,8,8-tetramethylnaphthalene-2-diselenide and ethyl 6-iodonicotinate.

$^1$H NMR/CDCl$_3$: 1.28 (s, 6H), 1.43 (s, 6H), 1.67 (m, 4H), 5.07 (s, 2H), 7.00 (d, 1H), 7.04 (d, 1H), 7.32 to 7.44 (m, 6H), 7.96 (dd, 1H), 9.06 (d, 1H).

Example 36

3-Methoxy-4-(3-benzyloxy-5,6,7,8-tetrahydro-5,5,8,8-tetramethyl-2-naphthylselanyl)benzoic acid a) 3-Hydroxy-5,6,7,8-tetrahydro-5,5,8,8-tetramethylnaphthalene-2-diselenide The product of Example 23(a), 3-methoxyethoxymethoxy-5,6,7,8-tetrahydro-5,5,8,8-tetramethylnaphthalene-2-diselenide, is treated in a manner similar to that of Example 31(c) to give the expected compound in the form of a yellow solid (100%).

b) 3-Benzyloxy-5,6,7,8-tetrahydro-5,5,8,8-tetramethylnaphthalene-2-diselenide

The product above is treated in a manner similar to that of Example 33(b).

c) 3-Methoxy-4-(3-benzyloxy-5,6,7,8-tetrahydro-5,5,8,8-tetramethyl-2-naphthylselanyl)benzoic acid The product is obtained in a manner similar to that of Example 7, starting with 3-benzyloxy5,6,7,8-tetrahydro-5,5,8,8-tetramethylnaphthalene-2-diselenide and ethyl 4-iodo-3-methoxybenzoate.

$^1$H NMR/CDCl$_3$: 1.22 (s, 6H), 1.25 (s, 6H), 1.67 (s, 4H), 3.97 (s, 3H), 5.07 (s, 2H), 6.89 (d, 1H), 6.90 (d, 1H), 7.22 to 7.25 (m, 5H), 7.50 to 7.53 (m, 3H).

Example 37

6-(3-Benzyloxy-5,6,7,8-tetrahydro-5,5,8,8-tetramethyl-2-naphthylselanyl)nicotinic acid The product is obtained in a manner similar to that of Example 7, starting with 3-benzyloxy5,6,7,8-tetrahydro-5,5,8,8-tetramethylnaphthalene-2 diselenide and ethyl 6-iodonicotinate $^1$H NMR/acetone D$_6$, CDCl$_3$: 1.25 (s, 6H), 1.27 (s, 6H) 1.68 (s, 4H), 5.08 (s, 2H), 6.94 (s, 1H), 7.04 (d, 1H), 7.31 (s, 3H), 7.62 (s, 1H), 7.94 (dd, 1H), 9.04 (d, 1H).

Example 38

4-(3-Hexyloxy-5,6,7,8-tetrahydro-5,5,8,8-tetramethyl-2-naphthylselanyl)-3-methoxybenzoic acid a) 3-Hexyloxy-5,6,7,8-tetrahydro-5,5,8,8-tetramethylnaphthylene-2-diselenide 60% sodium hydride (225 mg, 5.63 mmol) is added portionwise to a solution of 4-hydroxy-5,6,7,8-tetrahydro- 5,5,8,8-tetramethylnaphthalene-2-diselenide (1.2 g, 2.56 mmol) in 15 ml of THF and 15 ml of THF. Stirring is continued for 30 min at room temperature after the end of the addition, and iodohexane (1 ml, 6.8 mmol) is then added. The reaction medium is stirred for 4 h at room temperature and is then treated with water and ethyl ether. The organic phase is washed with water, dried over magnesium sulphate and concentrated. After purification by chromatography on silica (95 heptane/5 $CH_2Cl_2$), the product is obtained in the form of a yellow oil.

$^1$H NMR/CDCl$_3$: 0.90 (m, 9H); 1.30 to 1.48 (m, 12H); 1.59 (m, 4H); 1.77 (m, 2H); 3.85 (t, 2H); 6.92 (d, 1H); 7.17 (d, 1H).

b) 4-(3-Hexyloxy-5,6,7,8-tetrahydro-5,5,8,8-tetramethyl-2-naphthylselanyl)-3-methoxybenzoic acid The product is obtained in a manner similar to that of Example 7, starting with 3-hexyloxy-5,6,7,8-tetrahydro-5,5,8,8-tetramethylnaphthalene-2-diselenide and ethyl 4-iodo-3-methoxybenzoate.

$^1$H NMR/CDCl$_3$: 0.89 (t, 3H), 1.27 (s, 6H), 1.30 to 1.37 (m, 4H), 1.42 (s, 6H), 1.48 (m, 2H), 1.63 (m, 4H), 1.82 (m, 2H), 3.90 (t, 2H), 3.98 (s, 3H), 6.91 (d, 1H), 6.93 (s, 1H), 7.24 (s, 1H), 7.49 to 7.55. (m, 2H).

Example 39

6-(3-Hexyloxy-5,6,7,8-tetrahydro-5,5,8,8-tetramethyl-2-naphthylselanyl)nicotinic acid The product is obtained in a manner similar to that of Example 7, starting with 3-hexyloxy-5,6,7,8-tetrahydro-5,5,8,8-tetramethylnaphthalene-2-diselenide and ethyl 6-iodonicotinate.

$^1$H NMR/CDCl$_3$: 0.89 (t, 3H), 1.27 (s, 6H), 1.30 to 1.37 (m, 4H), 1.42 (s, 6H), 1.48 (m, 2H), 1.63 (m, 4H), 1.84 (m, 2H), 3.92 (t, 2H), 6.97 (d, 1H), 7.08 (d, 1H), 7.29 (d, 1H), 8.00 (dd, 1H), 9.08 (d, 1H).

Example 40

4-(5-Adamantan-1-yl-4-benzyloxy-2-methylphenylselenalyl)benzoic acid a) 5-Adamantan-1-yl-4-benzyloxy-2-methylphenyl diselenide The procedure is identical to that followed for Example 31(c) and 31(d), applied to the product of Example 16(a).

b) 4-(5-Adamantan-1-yl-4-benzyloxy-2-methylphenylselenalyl)benzoic acid

The product is obtained in a manner similar to that of Example 7, starting with 5-adamantan-1-yl-4-benzyloxy-2-methylphenyl diselenide and ethyl 4-iodobenzoate.

$^1$H NMR/acetone D$_6$, CDCl$_3$: 1.70 (s, 6H); 2.02 (s, 3H), 2.11 (s, 6H), 2.41 (s, 3H), 5.16 (s, 2H), 6.85 (dd, 1H), 6.98 (s, 1H), 7.35 to 7.58 (m, 6H), 7.97 (dd, 2H), 9.05 (d, 1H).

Example 41

Ethyl 6-[3-[5-(tert-butyldimethylsilanyloxy)pentylox-methyl]-5,6,7,8-tetrahydro-5,5,8,8-tetramethyl 2-naphthylselanyl)nicotinate a) 5-(3-Bromo-5,5,8,8-tetramethyl-5,6,7,8-tetrahydro- 2-naphthyloxy)pentyl acetate A solution of 3-bromo-5,5,8,8-tetramethyl-5,6,7,8-tetrahydronaphthalen-2-ol (10 g, 0.35 mol), 5-bromopentyl acetate (8.15 g) and potassium carbonate (33.6 g) in methyl ethyl ketone (200 ml) is refluxed for 2 hours. The reaction medium is treated with water and ethyl acetate. After separation of the phases by settling, the organic phase is washed twice with water, dried over magnesium sulphate and concentrated on a rotary evaporator under vacuum at 40° C. The product is purified by flash chromatography on a column of silica. Yellow oil. Yield: 93%.

b) [5-(3-Bromo-5,5,8,8-tetramethyl-5,6,7,8-tetrahydro-2-naphthyloxy)pentyloxy]-tert-butyldimethylsilane The acetate obtained above is saponified and the resulting hydroxyl group is then protected according to the following procedure: tert-butyldimethylsilyl chloride (2.64 g) is added to a mixture of 5-(3-bromo-5,5,8,8-tetramethyl-5,6,7,8-tetrahydro-2-naphthyloxy)pentan-1-ol (4.3 g, 11.7 mmol) and 80% sodium hydride (422 mg) in THF (20 ml).

The mixture is stirred at room temperature for 2 h. The solution is poured into a mixture of water and ethyl acetate. The organic phase is washed twice with water, dried over magnesium sulphate and concentrated on a rotary evaporator under vacuum at 40° C. The product is purified by flash chromatography on a column of silica.

Yellow oil. Yield: 64%.

c) 3-[5-(tert-Butyldimethylsilanyloxy)pentyloxy]-5,5,8,8-tetramethyl-5,6,7,8-tetrahydronaphthalene 2-diselenide The expected product is obtained from the bromo derivative obtained above, in a manner similar to that of Example 1a. Yellow oil. Yield: 10%.

d) Ethyl 6-[3-[5-(tert-butyldimethylsilanyloxy)pentyloxy]-5,6,7,8-tetrahydro-5,5,8,8-tetramethyl-2-naphthylselanyl]nicotinate In a manner similar to that of Example 1(b), by reaction of 257 mg (0.27 mmol) of the diselenide obtained above in 25 ml of ethanol with 119 mg of sodium borohydride, 120 mg (0.43 mmol) of ethyl 6-iodonicotinate and 4 mg of bis(bipyridine)nickel(II) dibromide, 152 mg (56%) of the expected derivative are obtained in the form of a yellow oil.

$^1$H NMR (CDCl$_3$): 0.00 (6H, s), 0.85 (9H, s), 1.22 (6H, s), 1.30 (6H, s), 1.33 to 1.50 (6H, m), 1.60 to 1.67 (7H, m), 3.48 (2H, t), 3.92 (2H, t), 4.35 (2H, q), 6.84 (1H, s), 6.99 (1H, d), 7.57 (1H, s), 7.91 (1H, dd), 8.97 (1H, d).

Example 42

6-[3-[5-(tert-Butyldimethylsilanyloxy)pentyloxy]-5,6,7,8-tetrahydro-5,5,8,8-tetramethyl-2-naphthylselanyl]nicotinic acid In a manner similar to that of Example 2, by reaction of 312 mg (0.49 mmol) of ethyl 6-[3-[5-(tert-butyldimethylsilanyloxy)pentyloxy]-5,6,7,8-tetrahydro-5,5,8,8-tetramethyl-2-naphthylselanyl]nicotinate with 213 mg (5.3 mmol) of sodium hydroxide in a THF/ethanol mixture (5 ml/5 ml), 210 mg (71%) of a yellow powder are obtained. m.p.: 161° C.

Example 43

6-[3-(5-Hydroxypentyloxy)-5,6,7,8-tetrahydro-5,5,8,8-tetramethyl-2-naphthylselanyl]nicotinic acid A mixture of the product from the above example (210 mg, 0.35 mmol), a 1M solution of tetra-n-butylammonium fluoride in THF (380 µl) in THF (5 ml) is stirred at room temperature for 3 h. 380 µl of the tetra-n-butylammonium fluoride solution are added to the reaction medium. Stirring is continued for 3.5 h and a further 380 µl of TBAF are added and the addition is continued for a further 1 h 20 min. The reaction medium is treated with 1N HCl solution and ethyl acetate. After separation of the phases by settling, the organic phase is washed with water, dried over anhydrous magnesium sulphate and concentrated. The product is purified by crystallization in a heptane/ethyl ether mixture. Mass: 194 mg, white powder. m.p.=190–192° C.

Example 44

Ethyl 4-(5,5,8,8-tetramethyl-5,6,7,8-tetrahydro-2-naphthylselanyl)benzoate (a) 5,6,7,8-Tetrahydro-5,5,8,8-tetramethylnaphthalene- 2-diselenide A 1.7M solution of tert-butyllithium in pentane (37.4 mmol, 22 ml) is added to a solution of 2-bromo-5,6,7,8-tetrahydro-5,5,8,8-tetramethyl-naphthalene (4.22 g, 15.8 mmol) in THF (100 ml) at −78° C. over 10 min. The mixture is stirred at 0° C. for 30 min. Selenium (1.33 g, 16.8 mmol) is added in 2 portions. The mixture is stirred at 0° C. for 15 min and then at room temperature for 30 min. 1N HCl solution (40 ml) is added and the reaction mixture is then treated with ethyl ether. The organic phase is washed twice with water, dried over anhydrous magnesium sulphate and concentrated on a rotary evaporator under vacuum at 40° C. 10 ml of ethanol and 50 mg of sodium hydroxide are added to the oil obtained. The mixture is stirred vigorously for a few minutes in air (until all the product has precipitated) and is then concentrated on a rotary evaporator under vacuum at 40° C. The solid obtained is filtered off on silica (eluting with heptane) and then crystallized from an ethanol/ether mixture.

Orange solid. Mass: 2.9 g. Yield: 69%.

$^1$H NMR (CDCl$_3$): 1.21 (6H, s), 1.25 (6H, s), 1.65 (4H, s), 7.20 (1H Ar, d, J=8.25 Hz), 7.38 (1H Ar, dd, J=1.9 Hz, J=8.25 Hz), 7.51 (1H Ar, d, J=1.9 Hz).

b) Ethyl 4-(5,5,8,8-tetramethyl-5,6,7,8-tetrahydro-2-naphthylselanyl)benzoate

In a manner similar to that of Example 1(b), by reaction of 213 mg (0.4 mmol) of the diselenide obtained above in 20 ml of ethanol with 73 mg of sodium borohydride (1.92 mmol), 177 mg (0.64 mmol) of ethyl 4-iodobenzoate and 37 mg of tetrakis(triphenylphosphine)palladium, and after purification by flash chromatography (70 heptane/30 CH$_2$Cl$_2$), 151 mg of the expected derivative are obtained in the form of a yellow solid. m.p.=73° C.

1H NMR (CDCl$_3$): 1.26 (6H, s), 1.29 (6H, s), 1.37 (t, 3H), 1.70 (4H, s), 4.34 (q, 2H), 7.15 to 7.25 (m, 3H), 7.32 (1H, d), 7.44 (1H, d), 7.89 (1H, d).

Example 45

Ethyl 4-(3-methoxyethoxymethoxy-5,5,8,8-tetramethyl-5,6,7,8-tetrahydro-2-naphthylselanyl)benzoate In a manner similar to that of Example 1(b), by reaction of 3.35 g (4.5 mmol) of 3-methoxyethoxymethoxy-5,6,7,8-tetrahydro-5,5,8,8-tetramethylnaphthalene-2-diselenide in 100 ml of ethanol with 501 mg of sodium borohydride (13.5 mmol), 2.5 g (9 mmol) of ethyl 4-iodobenzoate and 90 mg of bis(bipyridine)nickel(II) dibromide, and after purification by flash chromatography (85 heptane/15 EtOAc), 2.58 g of the expected derivative are obtained in the form of a yellow oil (83%).

Example 46

Ethyl 4-(3-hydroxy-5,5,8,8-tetramethyl-5,6,7,8-tetrahydro-2-naphthylselanyl)benzoate A mixture of ethyl 4-(3-methoxyethoxymethoxy5,5,8,8-tetramethyl-5,6,7,8-tetrahydro-2-naphthylselanyl)benzoate (2.3 g, 4.4 mmol), concentrated sulphuric acid (475 µl), methanol (40 ml) and THF (20 ml)is stirred for 48 h at room temperature. The reaction medium is extracted with ethyl ether. The organic phase is washed twice with water, dried over magnesium sulphate and concentrated on a rotary evaporator under vacuum. The product is purified by crystallization from heptane. 2.06 g (97%) of the expected compound are obtained in the form of an orange-coloured powder. m.p.=113° C.

Example 47

4-(3-Hydroxy-5,5,8,8-tetramethyl-5,6,7,8-tetrahydro-2-naphthylselanyl)benzoic acid In a manner similar to that of Example 2, by reaction of 400 mg (0.92 mmol) of ethyl 4-(3-hydroxy-5,5,8,8-tetramethyl-5,6,7,8-tetrahydro-2-naphthylselanyl)benzoate with 336 mg (8.4 mmol) of sodium hydroxide in a THF/ethanol mixture (20 ml/20 ml), 214 mg (58%) of a pink powder are obtained. m.p.=217° C.

Example 48

Ethyl 6-(3-methoxyethoxymethoxy-5,5,8,8-tetramethyl-5,6,7,8-tetrahydro-2-naphthylselanyl)nicotinate In a manner similar to that of Example 1(b), by reaction of 3.35 g (4.5 mmol) of 3-methoxyethoxymethoxy-5,6,7,8- tetrahydro-5,5,8,8-tetramethylnaphthalene-2-diselenide in 100 ml of ethanol with 501 mg of sodium borohydride (13.5 mmol), 2.5 g (9 mmol) of ethyl 4-iodobenzoate and 90 mg of bis(bipyridine)nickel(II) dibromide, and after purification by flash chromatography.

(85 heptane/15 EtOAc), 2.09 g of the expected derivative are obtained in the form of a yellow oil (45%).

$^1$H NMR/CDCl$_3$: 1.25 (s, 6H), 1.31 (s, 6H), 1.38 (t, 3H), 1.69 (m, 4H), 3.36 (s, 3H), 3.50 (m, 2H), 3.73 (m, 2H), 4.37 (q, 2H), 5.22 (s, 2H), 7.01 (d, 1H), 7.22 (s, 1H), 7.60 (s, 1H), 7.94 (dd, 1H), 8.99 (d, 1H).

Example 49

Ethyl 6-(3-hydroxy-5,5,8,8-tetramethyl-5,6,7,8-tetrahydro-2-naphthylselanyl)nicotinate A mixture of ethyl 6-(3-methoxyethoxymethoxy5,5,8,8-tetramethyl-5,6,7,8-tetrahydro-2-naphthylselanyl)nicotinate (2.6 g, 5 mmol), concentrated sulphuric acid (535 µl), ethanol (75 ml) and THF (25 ml) is stirred for 3 days at room temperature. The reaction medium is extracted with ethyl ether. The organic phase is washed twice with water, dried over magnesium sulphate and concentrated on a rotary evaporator under vacuum. The solid obtained is washed with ethyl ether. 2.01 g (93%) of the expected compound are obtained in the form of an orange-coloured powder. m.p.=138° C.

Example 50

6-(3-Hydroxy-5,5,8,8-tetramethyl-5,6,7,8-tetrahydro-2-naphthylselanyl)nicotinic acid In a manner similar to that of Example 2, by reaction of 400 mg (0.92 mmol) of ethyl 6-(3-hydroxy-5,5,8,8-tetramethyl-5,6,7,8-tetrahydro-2-naphthylselanyl)nicotinate with 357 mg (8.9 mmol) of sodium hydroxide in a THF/ethanol mixture (20 ml/20 ml), 60 mg (16%) of a yellow powder are obtained. m.p.: 250° C.

Example 51

Ethyl 6-[3-(3-ethoxycarbonylpropoxy)-5,5,8,8-tetramethyl-5,6,7,8-tetrahydro-2-naphthylselanyl]-nicotinate 432 mg (102.0 mmol) of ethyl 6-(3-hydroxy-5,5,8,8-tetramethyl-5,6,7,8-tetrahydro 2-naphthylselanyl)nicotinate, 276 mg (2 mmol) of potassium carbonate and 390 mg (2 mmol) of ethyl 4-bromobutanoate are introduced into a three-necked flask. The mixture is heated at 80° C. for 12 h. The reaction medium is poured into water and extracted with ethyl ether, and the organic phase is separated out by settling, washed with water, dried over magnesium sulphate and evaporated. After purification by flash chromatography (9 heptane/1 EtOAc), 467 mg (85%) of the expected compound are collected in the form of an orange-coloured oil.

$^1$H NMR/CDCl$_3$: 1.20 to 1.31 (m, 15H), 1.38 (t, 3H), 1.69 (s, 4H), 1.96 (m, 2H), 2.38 (t, 2H), 2.85 (t, 2H), 4.12 (q, 2H), 4.3.6 (q, 2H), 6.88 (d, 1H), 7.02 (s, 1H), 7.48 (s, 1H), 8.26 (dd, 2H), 8.83 (d, 1H).

Example 52

6-[3-(3-Carboxypropoxy)-5,5,8,8-tetramethyl-5,6,7,8-tetrahydro-2-naphthylselanyl]nicotinic acid In a manner similar to that of Example 2, by reaction of 340 mg (0.62 mmol) of ethyl 6-[3-(3-ethoxycarbonylpropoxy)-5,5,8,8-tetramethyl-5,6,7,8-tetrahydro-2-naphthylselanyl]nicotinate with 250 mg (62.2 mmol) of sodium hydroxide in ethanol (10 ml), 211 mg (69%) of a white powder are obtained. m.p.: 177° C.

Example 53

Ethyl 4-[3-(3-ethoxycarbonylpropoxy)-5,5,8,8-tetramethyl-5,6,7,8-tetrahydro-2-naphthylselanyl)-benzoate In a manner similar to that of Example 51, by reaction of 300 mg (0.86 mmol) of ethyl 4-(3-hydroxy-5,5,8,8-tetramethyl-5,6,7,8-tetrahydro-2-naphthyl selanyl)benzoate with 336 mg (1.72 mmol) of ethyl 4-bromobutanoate and 238 mg of potassium carbonate in MEK (10 ml), 364 mg (78%) of a yellow oil are obtained.

$^1$H NMR/CDCl$_3$: 1.16 to 1.32 (m, 15H), 1.38 (t, 3H), 1.66 (m, 4H), 1.98 (m, 2H), 2.30 (t, 2H), 3.98 (t, 2H), 4.08 (q, 2H), 4.35 (q, 2H), 6.78 (s, 1H), 7.28 (s, 1H), 7.41 (dd, 2H), 7.87 (dd, 2H).

Example 54

4-[3-(3-Carboxypropoxy)-5,5,8,8-tetramethyl-5,6,7,8-tetrahydro-2-naphthylselanyl)benzoic acid In manner similar to that of Example 2, by reaction of 250 mg (0.46 mmol) of ethyl 4-[3-(3-carboxypropoxy)-5,5,8,8-tetramethyl-5,6,7,8-tetrahydro-2-naphthylselanyl]benzoate with 183 mg (4.6 mmol) of sodium hydroxide in a THF/ethanol mixture (5 ml/5 ml), 172 mg (76%) of a white powder are obtained. m.p.: 230° C.

Example 55

Ethyl 4-[3-(7-methoxycarbonylheptyloxy)-5,5,8,8-tetramethyl-5,6,7,8-tetrahydro-2-naphthylselanyl]benzoate In a manner similar to that of Example 51, by reaction of 370 mg (0.86 mmol) of ethyl 4-(3-hydroxy-5,5,8,8-tetramethyl-5,6,7,8-tetrahydro 2-naphthylselanyl)benzoate with 408 mg (1.72 mmol) of methyl 8-bromooctanoate and 238 mg of potassium carbonate in MEK (10 ml), 502 mg (99%) of a yellow oil are obtained.

$^1$H NMR/CDCl$_3$: 1.16 (s, 6H), 1.26 to 1.29 (m, 12H), 1.38 (t, 3H), 1.56 to 1.68 (m, 8H), 2.28 (t, 2H), 3.66 (s, 3H), 3.92 (t, 2H), 4.36 (q, 2H), 6.78 (s, 1H), 7.27 (s, 1H), 7.41 (dd, 2H), 7.88 (dd, 2H).

Example 56

4-[3-(7-Carboxyheptyloxy)-5,5,8,8-tetramethyl-5,6,7,8-tetrahydro-2-naphthylselanyl]benzoic acid In a manner similar to that of Example 2, by reaction of 410 mg (0.7 mmol) of ethyl 4-[3-(7-methoxycarbonylheptyloxy)-5,5,8,8-tetramethyl5,6,7,8-tetrahydro-2-naphthylselanyl]benzoate with 280 mg (7 mmol) of sodium hydroxide

Example 57

Ethyl 6-[3-(7-methoxycarbonylheptyloxy)-5,5,8,8-tetramethyl-5,6,7,8-tetrahydro-2-naphthylselanyl]-nicotinate In a manner similar to that of Example 51, by reaction of 460 mg (1.06 mmol) of ethyl 6-(3-hydroxy-5,5,8,8-tetramethyl-5,6,7,8-tetrahydro 2-naphthylselanyl)nicotinate with 515 mg (2.17 mmol) of methyl 8-bromooctanoate and 295 mg of potassium carbonate in MEK (10 ml), 487 mg (78%) of a yellow oil are obtained.

Example 58

6-[3-(7-Carboxyheptyloxy)-5,5,8,8-tetramethyl-5,6,7,8-tetrahydro-2-naphthylselanyl]nicotinic [lacuna]

In a manner similar to that of Example 2, by reaction of 390 mg (0.66 mmol) of ethyl 6-[3-(7-methoxycarbonylheptyloxy)-5,5,8,8-tetramethyl- 5,6,7,8-tetrahydro-2-naphthylselanyl]nicotinate with 265 mg (6.6 mmol) of sodium hydroxide in a THF/ethanol mixture (5 ml/1 ml), 277 mg (77%) of a white powder are obtained. m.p.: 186° C.

Example 59

Ethyl 6-(3-(2-acetoxyethoxy)-5,5,8,8-tetramethyl-5,6,7,8-tetrahydro-2-naphthylselanyl)nicotinate a) 2-Bromoethyl acetate Acetic anhydride (11.35 ml, 0.12 mol) is added dropwise to a solution of 2-bromoethanol (12.5 g, 0.1 mol) and DMAP (1.22 g) in 125 ml of dichloromethane. The mixture is stirred at room temperature for 12 h and treated with water and dichloromethane. The organic phase is washed with water, dried over magnesium sulphate, concentrated on a rotary evaporator and purified by distillation.

Yellowish liquid (94%).

b) Ethyl 6-(3-(2-acetoxyethoxy)-5,5,8,8-tetramethyl-5,6,7,8-tetrahydro-2-naphthylselanyl)nicotinate In a manner similar to that of Example 51, by reaction of 477 mg (1.10 mmol) of ethyl 6-(3-hydroxy-5,5,8,8-tetramethyl-5,6,7,8-tetrahydro 2-naphthylselanyl)nicotinate with 396 mg (2.2 mmol) of 2-bromoethyl acetate and 304 mg of potassium carbonate in MEK (10 ml), 545 mg (96%) of a yellow oil are obtained.

$^1$H NMR/CDCl$_3$: 1.24 (s, 6H), 1.32 (s, 6H), 1.38 (t, 3H), 1.69 (s, 4H), 1.99 (s, 3H), 3.00 (t, 3H), 4.24 (t, 2H), 4.38 (q, 2H), 6.89 (d, 1H), 7.03 (s, 1H), 7.54 (s, 1H), 8.27 (dd, 1H), 8.83 (d, 1H).

Example 60

6-(3-(2-Hydroxyethoxy)-5,5,8,8-tetramethyl-5,6,7,8-tetrahydro-2-naphthylselanyl)nicotinic acid In a manner similar to that of Example 2, by reaction of 419 mg (0.81 mmol) of ethyl 6-[3-(2-acetoxyethoxy)-5,5,8,8-tetramethyl-5,6,7,8-tetrahydro-2-naphthylselanyl]nicotinate with 320 mg (8 mmol) of sodium hydroxide in a THF/ethanol mixture (4 ml/4 ml), 273 mg (75%) of a white powder are obtained. m.p.: 170° C.

Example 61

Ethyl 4-(3-(2-acetoxyethoxy)-5,5,8,8-tetramethyl-5,6,7,8-tetrahydro-2-naphthylselanyl)benzoate In a manner similar to that of Example 51, by reaction of 400 mg (0.93 mmol) of ethyl 4-(3-hydroxy-5,5,8,8-tetramethyl-5,6,7,8-tetrahydro-2-naphthylselanyl)benzoate with 334 mg (2.2 mmol) of 2-bromoethyl acetate and 257 mg of potassium carbonate in MEK (10 ml), 333 mg (69%) of a yellow oil are obtained.

$^1$H NMR/CDCl$_3$: 1.16 (s, 6H), 1.29 (s, 6H), 1.38 (t, 3H), 1.59 (s, 4H), 1.99 (s, 3H), 4.16 (m, 2H), 4.29 to 4.40 (m, 4H), 6.82 (s, 1H), 7.28 (s, 1H), 7.43 (d, 1H), 7.89 (d, 1H).

Example 62

4-(3-(2-Hydroxyethoxy)-5,5,8,8-tetramethyl-5,6,7,8-tetrahydro-2-naphthylselanyl)benzoic acid In a manner similar to that of Example 2, by reaction of 322 mg (0.62 mmol) of ethyl 4-[3-(2-acetoxyethoxy)-5,5,8,8-tetramethyl-5,6,7,8-tetrahydro-2-naphthylselanyl]benzoate with 250 mg (6.2 mmol) of sodium hydroxide in a THF/ethanol mixture (3 ml/3 ml), 226 mg (81%) of a white powder are obtained. m.p.: 197° C.

Example 63

Ethyl 4-(3-(2-chloroethoxy)-5,5,8,8-tetramethyl-5,6,7,8-tetrahydro-2-naphthylselanyl)benzoate In a manner similar to that of Example 51, by reaction of 431 mg (1 mmol) of ethyl 4-(3-hydroxy5,5,8,8-tetramethyl-5,6,7,8-tetrahydro 2-naphthylselanyl benzoate with 222 mg (1.5 mmol) of 1-bromo-2-chloroethyl [lacuna] and 278 mg of potassium carbonate in MEK (20 ml), 200 mg (40%) of a yellow oil are obtained.

Example 64

Ethyl 4-[3-(2-iodoethoxy)-5,5,8,8-tetramethyl-5,6,7,8-tetrahydro-2-naphthylselanyl]benzoate A mixture of 200 mg (0.4 mmol) of ethyl 4-[3-(2-chloroethoxy)-5,5,8,8-tetramethyl-5,6,7,8-tetrahydro-2-naphthylselanyl]benzoate with 607 mg (4 mmol) of sodium iodide in MEK (4 ml) is refluxed for 12 h. The reaction medium is treated with water and ethyl ether. The organic phase is washed with water, dried over magnesium sulphate and concentrated on a rotary evaporator. The oil obtained is reacted under the same conditions. 159 mg (68%) of a yellow solid are obtained. m.p.=87° C.

Example 65

6-(3-Adamantan-1-yl-4-methoxyphenylselanyl)nicotinic acid

The product is obtained in a manner similar to that of Example 7, starting with 3-adamantan-1-yl-4-methoxyphenyl diselenide and ethyl 6-iodonicotinate.

$^1$H NMR/THF D8: 1.79 (s, 6H), 2.04 (s, 3H), 2.13 (s, 6H), 3.89 (s, 3H), 6.93 (d, 1H), 7.02 (d, 1H), 7.52 to 7.55 (m, 2H), 7.91 (dd, 1H), 8.9 (d, 1H).

Example 66

[6-(3,5,5,8,8-Pentamethyl-5,6,7,8-tetrahydro-2-naphthylselanyl)-3-pyridyl]methanol 3 g (7 mmol) of ethyl 6-(3,5,5,8,8-pentamethyl-5,6,7,8-tetrahydro-2-naphthylselanyl) nicotinate, 800 mg (20 mmol) of lithium aluminium hydride and 90 ml of THF are introduced into a round-bottomed flask under a stream of nitrogen. The reaction medium is refluxed for two hours, cooled, the excess hydride is hydrolysed and the salt is filtered off. After evaporation of the filtrate, the residue obtained is recrystallized from heptane. 1.36 g (50%) of [6-(3,5,5,8,8-pentamethyl-5,6,7,8-tetrahydro-2-naphthylselanyl)-3-pyridyl]methanol with a melting point of 110–111° C. are collected.

Example 67

N-Ethyl-6-(3,5,5,8,8-pentamethyl-5,6,7,8-tetrahydro-2-naphthylselanyl)nicotinamide (a) 6-(3,5,5,8,8-Pentamethyl-5,6,7,8-tetrahydro-2-naphthylselanyl)nicotinyl chloride 2 g (5 mmol) of 6-(3,5,5,8,8-pentamethyl-5,6,7,8-tetrahydro-2-naphthylselanyl)nicotinic acid, 20 ml of toluene, 100 µl of DMF and 450 µl of thionyl chloride are introduced into a round-bottomed flask. The reaction medium is refluxed for one hour and evaporated. 100% of the expected acid chloride are collected, this product being used for the rest of the synthesis without further purification.

(b) N-Ethyl-6-(3,5,5,8,8-pentamethyl-5,6,7,8-tetrahydro-2-naphthylselanyl)nicotinamide By reaction of 2.1 g (5 mmol) of the above acid chloride with 1 ml of ethylamine (70% in water) in 20 ml of THF, 2.02 g (95%) of the expected amide, with a melting point of 218–220° C., are obtained.

Example 68

Morpholin-4-yl-[6-(3,5,5,8,8-pentamethyl-5,6,7,8-tetrahydro-2-naphthylselanyl)-3-pyridyl]methanone By reaction of 2.1 g (5 mmol) of the above acid chloride with 1 ml of morpholine in 20 ml of THF, 2.17 g (93%) of the expected amide, with a melting point of 147–148° C., are obtained.

Example 69

N-(4-Hydroxyphenyl)-6-(3,5,5,8,8-pentamethyl-5,6,7,8-tetrahydro-2-naphthylselanyl)nicotinamide By reaction of 2.1 g (5 mmol) of the above acid chloride with 540 mg (5 mmol) of 4-aminophenol in 40 ml of THF in the presence of 830 µl of triethylamine, 2.35 g (96%) of the expected amide, with a melting point of 223–225° C., are obtained.

Example 70

6-(3,5,5,8,8-Pentamethyl-5,6,7,8-tetrahydro-2-naphthylselanyl)pyridine-3-carbaldehyde By reaction of 890 mg (2.3 mmol) of [6-(3,5,5,8,8-pentamethyl-5,6,7,8-tetrahydro-2-naphthylselanyl)-3-pyridyl]methanol with 1.12 g (3 mmol) of pyridinium dichromate in 90 ml of dichloromethane, and after filtration on silica, 600 mg (68%) of 6-(3,5,5,8,8-pentamethyl-5,6,7,8-tetrahydro-2-naphthylselanyl)pyridine-3-carbaldehyde, with a melting point of 150–152° C., are obtained.

B. FORMULATION EXAMPLES

1) Oral Route (a) The following composition is prepared in the form of a 0.8 g tablet

| | |
|---|---|
| Compound of Example 3 | 0.005 g |
| Pregelatinized starch | 0.265 g |
| Microcrystalline cellulose | 0.300 g |
| Lactose | 0.200 g |
| Magnesium stearate | 0.030 g |

For the treatment of acne, 1 to 3 tablets will be administered to an adult individual per day for 3 to 6 months, depending on the severity of the case treated.

(b) A drinkable suspension for packaging in 5 ml vials is prepared:

| | |
|---|---|
| Compound of Example 12 | 0.050 g |
| Glycerol | 0.500 g |
| 70% sorbitol | 0.500 g |
| Sodium saccharinate | 0.010 g |
| Methyl parahydroxybenzoate | 0.040 g |
| Flavouring | qs |
| Purified water | qs 5 ml |

For the treatment of acne, 1 vial will be administered to an adult individual per day for 3 months, depending on the severity of the case treated.

(c) The following formulation for packaging in gelatin capsules is prepared:

| | |
|---|---|
| Compound of Example 5 | 0.025 g |
| Corn starch | 0.060 g |
| Lactose qs | 0.300 g |

The gelatin capsules used consist of gelatin, titanium oxide and a preserving agent.

In the treatment of psoriasis, 1 gelatin capsule will be administered to an adult individual per day for 30 days.

2) Topical Route (a) The following nonionic water-in-oil cream is prepared:

| | |
|---|---|
| Compound of Example 23 | 0.100 g |
| Mixture of emulsifying lanolin alcohols, waxes and refined oils, sold by the company BDF under the name "anhydrous Eucerin" | 39.900 g |
| Methyl para-hydroxybenzoate | 0.075 g |
| Propyl para-hydroxybenzoate | 0.075 g |
| Sterile demineralized water qs | 100.000 g |

This cream will be applied to psoriatic skin once or twice a day for 30 days.

(b) A gel is prepared by making the following formulation:

| | |
|---|---|
| Compound of Example 39 | 0.050 g |
| Base erythromycin | 4.000 g |
| Butylhydroxytoluene | 0.050 g |
| Hydroxypropylcellulose sold by the company Hercules under the name "Klucel HF" | 2.000 g |
| Ethanol (at 95°) qs | 100.000 g |

This gel will be applied to skin affected with dermatitis or acneic skin 1 to 3 times a day for 6 to 12 weeks, depending on the severity of the case treated.

(c) An anti-seborrhoeic lotion is prepared by mixing together the following ingredients:

| | |
|---|---|
| Compound of Example 6 | 0.030 g |
| Propylene glycol | 5.000 g |
| Butylhydroxytoluene | 0.100 g |
| Ethanol (at 95°) qs | 100.000 g |

This lotion will be applied twice a day to a seborrhoeic scalp, and a significant improvement is observed within a period of between 2 and 6 weeks.

(d) A cosmetic composition to combat the harmful effects of the sun is prepared by mixing together the following ingredients:

| | |
|---|---|
| Compound of Example 59 | 1.000 g |
| Benzylidenecamphor | 4.000 g |
| Fatty acid triglycerides | 31.000 g |
| Glyceryl monostearate | 6.000 g |
| Stearic acid | 2.000 g |
| Cetyl alcohol | 1.200 g |
| Lanolin | 4.000 g |
| Preserving agents | 0.300 g |
| Propylene glycol | 2.000 g |
| Triethanolamine | 0.500 g |
| Fragrance | 0.400 g |
| Demineralized water qs | 100.000 g |

This composition will be applied daily and makes it possible to combat light-induced ageing.

(e) The following nonionic oil-in-water cream is prepared:

| | |
|---|---|
| Compound of Example 16 | 0.500 g |
| Vitamin D3 | 0.020 g |
| Cetyl alcohol | 4.000 g |
| Glyceryl monostearate | 2.500 g |
| PEG-50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water qs | 100.000 g |

This cream will be applied to psoriatic skin once or twice a day for 30 days.

(f) A topical gel is prepared by mixing together the following ingredients:

| | |
|---|---|
| Compound of Example 4 | 0.050 g |
| Ethanol | 43.000 g |
| α-tocopherol | 0.050 g |
| Carboxyvinyl polymer sold under the name "Carbopol 941" by the company "Goodrich" | 0.500 g |
| Triethanolamine as an aqueous solution at 20% by weight | 3.800 g |
| Water | 9.300 g |
| Propylene glycol qs | 100.000 g |

This gel will be applied in the treatment of acne 1 to 3 times a day for 0.6 to 12 weeks, depending on the severity of the case treated.

(g) A hair lotion to combat hair loss and to promote regrowth of the hair is prepared by mixing together the following ingredients:

| | |
|---|---|
| Compound of Example 31 | 0.05 g |
| Compound sold under the name "Minoxidil" | 1.00 g |
| Propylene glycol | 20.00 g |
| Ethanol | 34.92 g |
| Polyethylene glycol (molecular mass = 400) | 40.00 g |
| Butylhydroxyanisole | 0.01 g |
| Butylhydroxytoluene | 0.02 g |
| Water qs | 100.00 g |

This lotion will be applied twice a day for 3 months to a scalp which has suffered considerable hair loss.

(h) An anti-acne cream is prepared by mixing together the following ingredients:

| | |
|---|---|
| Compound of Example 7 | 0.050 g |
| Retinoic acid | 0.010 g |
| Mixture of glycerol stearate and polyethylene glycol stearate (75 mol), sold under the name "Gelot 64" by the company "Gattefosse" | 15.000 g |
| Kernel oil polyoxyethylenated with 6 mol of ethylene oxide, sold under the name "Labrafil M2130 CS" by the company "Gattefosse" | 8.000 g |
| Perhydrosqualene | 10.000 g |
| Preserving agents | qs |
| Polyethylene glycol (molecular mass = 400) | 8.000 g |
| Disodium salt of ethylenediaminetetraacetic acid | 0.050 g |
| Purified water qs | 100.000 g |

This cream will be applied to skin affected with dermatitis or to acneic skin 1 to 3 times a day for 6 to 12 weeks.

(i) An oil-in-water cream is prepared by making the following formulation:

| | |
|---|---|
| Compound of Example 43 | 0.020 g |
| Betamethasone 17-valerate | 0.050 g |
| S-Carboxymethylcysteine | 3.000 g |
| Polyoxyethylene stearate (40 mol of ethylene oxide) sold under the name "Myrj 52" by the company "Atlas" | 4.000 g |

-continued

| | |
|---|---|
| Sorbitan monolaurate, polyoxyethylene with 20 mol of ethylene oxide, sold under the name "Tween 20" by the company "Atlas" | 1.800 g |
| Mixture of glyceryl mono- and distearate sold under the name "Geleol" by the company "Gattefosse" | 4.200 g |
| Propylene glycol | 10.000 g |
| Butylhydroxyanisole | 0.010 g |
| Butylhydroxytoluene | 0.020 g |
| Cetostearyl alcohol | 6.200 g |
| Preserving agents | qs |
| Perhydrosqualene | 18.000 g |
| Mixture of caprylic/capric triglycerides sold under the name "Miglyol 812" by the company "Dynamit Nobel" | 4.000 g |
| Triethanolamine (99% by weight) | 2.500 g |
| Water qs | 100.000 g |

This cream will be applied twice a day to skin affected with dermatitis, for 30 days.

(j) The following oil-in-water cream is prepared:

| | |
|---|---|
| Lactic acid | 5.000 g |
| Compound of Example 1 | 0.020 g |
| Polyoxyethylene stearate (40 mol of ethylene oxide) sold under the name "Myrj 52" by the company "Atlas" | 4.000 g |
| Sorbitan monolaurate, polyoxyethylene with 20 mol of ethylene oxide, sold under the name "Tween 20" by the company "Atlas" | 1.800 g |
| Mixture of glyceryl mono- and distearate sold under the name "Geleol" by the company "Gattefosse" | 4.200 g |
| Propylene glycol | 10.000 g |
| Butylhydroxyanisole | 0.010 g |
| Butylhydroxytoluene | 0.020 g |
| Cetostearyl alcohol | 6.200 g |
| Preserving agents | qs |
| Perhydrosqualene | 18.000 g |
| Mixture of caprylic/capric triglycerides sold under the name "Miglyol 812" by the company "Dynamit Nobel" | 4.000 g |
| Water qs | 100.000 g |

This cream will be applied once a day and helps to combat ageing, whether this is light-induced or chronological ageing.

What is claimed is:

1. A compound having formula (I):

$$\text{(I)}$$

in which:
$R_1$ is COOH;
Ar is $R_2$ and $R_3$, with the carbon atoms from which they attach, form a 6-membered saturated ring;
$R_4$ is a lower alkyl radical;
$R_7$ represents a hydrogen atom, a halogen atom, a lower alkyl radical, a nitro radical, a radical $OR_{13}$, a polyether radical or a radical of the following formula:

$$\diagdown N \diagup^{R_{15}}_{R_{14}}$$

$R_{13}$ represents a hydrogen atom or a lower alkyl radical;
$R_{14}$ and $R_{15}$, which may be identical or different, represent a hydrogen atom or a lower alkyl radical;
or a salt or isomer thereof.

2. A salt of a compound according to claim 1, said salt being an alkali metal or alkaline-earth metal salt, zinc or organic amine salt, or a salt of an inorganic or organic acid.

3. A compound according to claim 1, containing a lower alkyl radical selected from the group consisting of methyl, ethyl, isopropyl, butyl, and tert-butyl radicals.

4. A compound according to claim 1, containing a polyether radical selected from the group consisting of methoxymethyl ether, methoxyethoxymethyl ether, and methylthiomethyl ether radicals.

5. A compound according to claim 1, selected from the group consisting of:
6-(3,5,5,8,8-pentamethyl-5,6,7,8-tetrahydro-2-naphthylselanyl)nicotinic acid,
6-(5,5,8,8-tetramethyl-3-propoxy-5,6,7,8-tetrahydro-2-naphthylselanyl)nicotinic acid,
6-(5,5,8,8-tetramethyl-5,6,7,8-tetrahydro-2-naphthylselanyl)nicotinic acid,
6(4-methoxyethoxymethoxy-5,5,8,8-tetramethyl-5,6,7,8-tetrahydro-2-naphthylselanyl)nicotinic acid,
6-(4-methoxymethoxy-5,5,8,8-tetramethyl-5,6,7,8-tetrahydro-2-naphthylselanyl)nicotinic acid,
6-(3-methoxyethoxymethoxy-5,5,8,8-tetramethyl-5,6,7,8-tetrahydro-2-naphthylselanyl)nicotinic acid,
2-(3-methoxyethoxymethoxy-5,5,8,8-tetramethyl-5,6,7,8-tetrahydro-2-naphthylselanyl]nicotinic acid,
6-[3-(5-hydroxypentyloxy)-5,5,8,8-tetramethyl-5,6,7,8-tetrahydro-2-naphthylselanyl]nicotinic acid,
6-(3-hydroxy-5,5,8,8-tetramethyl-5,6,7,8-tetrahydro-2-naphthylselanyl)nicotinic acid,
6-[3-(3-carboxypropoxy)-5,5,8,8-tetramethyl-5,6,7,8-tetrahydro-2-naphthylselanyl]nicotinic acid,
6-[3-(7-carboxyheptyloxy)-5,5,8,8-tetramethyl-5,6,7,8-tetrahydro-2-naphthylselanyl]nicotinic acid, and
6-[3-(2-hydroxyethoxy)-5,5,8,8-tetramethyl-5,6,7,8-tetrahydro-2-naphthylselanyl]nicotinic acid.

6. Cosmetic composition comprising, in a cosmetically acceptable support, at least one compound as defined in claim 1.

7. Composition according to claim 6, wherein the concentration of compound(s) is between 0.001% and 3% by weight relative to the composition as a whole.

8. A method for body or hair hygiene comprising administering an effective amount of the cosmetic composition according to claim 6 to a subject.

* * * * *